US006285902B1

(12) United States Patent
Kienzle, III et al.

(10) Patent No.: US 6,285,902 B1
(45) Date of Patent: Sep. 4, 2001

(54) COMPUTER ASSISTED TARGETING DEVICE FOR USE IN ORTHOPAEDIC SURGERY

(75) Inventors: Thomas C. Kienzle, III, Wilton, CT (US); Jon T. Lea, Lake Bluff, IL (US)

(73) Assignee: Surgical Insights, Inc., Evanston, IL (US)

( * ) Notice: Subject to any disclaimer, the term of this patent is extended or adjusted under 35 U.S.C. 154(b) by 0 days.

(21) Appl. No.: 09/248,133

(22) Filed: Feb. 10, 1999

(51) Int. Cl.$^7$ ........................................... A61B 6/00
(52) U.S. Cl. ..................... 600/427; 606/130; 378/20; 378/205
(58) Field of Search ..................... 600/426, 427; 606/130; 356/141.1, 375; 378/20, 205, 206, 207, 21; 128/849, 853, 856

(56) References Cited

U.S. PATENT DOCUMENTS

| | | |
|---|---|---|
| 4,791,934 | 12/1988 | Brunnett . |
| 5,230,623 | 7/1993 | Guthrie et al. . |
| 5,251,127 | 10/1993 | Raab . |
| 5,305,203 | 4/1994 | Raab . |
| 5,309,913 | 5/1994 | Kormos et al. . |
| 5,383,454 | 1/1995 | Bucholz . |
| 5,409,001 | 4/1995 | Seyler et al. . |
| 5,445,166 | 8/1995 | Taylor . |

(List continued on next page.)

OTHER PUBLICATIONS

Hamadeh, et al., "Toward automatic registration between CT and X–ray images; cooperation between 3D/2D registration and 2D edge detection," Second Annual International Symposium on Medical Robotics and Computer Assisted Surgery, Baltimore, Nov. 4–7, 1995.

Flashpoint Model 5000 3D Localizer, User's & Programmer's Manual, Image Guided Technologies, Inc., Boulder, CO, Chapter 7, no copyright date (but received by us in 1997).

Joskowicz, Leo et al., "FRACAS: A System For Computer–Aided Image–Guided Long Bone Fracture Surgery," Computer Aided Surgery, May 26, 1999.

Potamianos, P., et al, "Intra–Operative Imaging Guidance For Keyhole Surgery—Methodology and Calibration," Proceedings of the First International Symposium on Medical Robotics and Computer Assisted Surgery, Pittsburg, PA, Sep. 22–24, 1994, pp. 98–104.

Potamianos, P., et al, Intra–Operative Registration For Percutaneous Surgery, Proceedings of the Second Annual International Symposium on Medical Robotics and Computer Assisted Surgery, Baltimore, MD, Nov. 4–7, 2000.

(List continued on next page.)

Primary Examiner—Marvin M. Lateef
Assistant Examiner—Eleni Mantis Mercader
(74) Attorney, Agent, or Firm—Bullwinkel Partners, Ltd

(57) ABSTRACT

An image guided surgery system to enable a surgeon to move a surgical tool into a desired position relative to a body part is provided. The system works by accurately superimposing representations of the tool being used in the surgical field over images of the body part such that real-time tool position feedback is provided to the surgeon. The system uses a fluoroscopic x-ray device to generate two-dimensional body part images, a localizing device to determine the poses of surgical tools and the x-ray device, mathematical modeling of the imaging chain of the x-ray device, and a means for displaying the images of the body part superimposed with representations of the surgical tools. A related feature is the use of a digital flat-panel x-ray imager that employs a regular array of sensors to convert incident x-ray energy to a computer readable image, thereby permitting the fluoroscopic x-ray device to be used in any orientation without being affected by distortions due to local magnetic fields.

54 Claims, 18 Drawing Sheets

U.S. PATENT DOCUMENTS

| | | |
|---|---|---|
| 5,490,524 | 2/1996 | Williams et al. . |
| 5,517,990 | 5/1996 | Kalfas et al. . |
| 5,617,857 * | 4/1997 | Chader et al. ............... 128/653.1 |
| 5,622,170 | 4/1997 | Schulz . |
| 5,638,819 | 6/1997 | Manwaring et al. . |
| 5,682,886 * | 11/1997 | Delp et al. ................. 128/653.1 |
| 5,755,725 | 5/1998 | Druais . |
| 5,769,861 * | 6/1998 | Vilsmeier ...................... 606/130 |
| 5,772,594 | 6/1998 | Barrick . |
| 5,799,055 | 8/1998 | Peshkin . |
| 5,836,954 | 11/1998 | Heilbrun et al. . |
| 5,841,830 | 11/1998 | Barni . |
| 5,848,967 | 12/1998 | Cosman . |
| 5,904,691 | 5/1999 | Barnett . |
| 5,912,943 * | 7/1999 | Deucher et al. ................ 378/98.8 |
| 6,006,126 | 12/1999 | Cosman . |
| 6,006,127 | 12/1999 | Van Der Brug . |
| 6,031,888 | 2/2000 | Ivan . |
| 6,041,097 | 3/2000 | Roos . |
| 6,092,928 * | 7/2000 | Mattson et al. ................. 378/205 |

OTHER PUBLICATIONS

Lavalee, et al.; Computer Assisted Spine Surgery: a technique for accurate transpedicular screw fixation using CT data and a 3–D analyzer; *Proceedings of the First International Symposium on Medical Robotics and Computer Assisted Surgery*; Pittsburgh, PA; 9/22–24/94.

Viant, et al., A Computer Assisted Orthopaedic System for Distal Locking Intramedullary Nails; *Medimec '95*, Bristol, UK; 9/95.

Ryan, et al.; Frameless Sterotaxy with Real–Time Tracking of Patient Head Movement and Retrospective Patient–Image Registration; *Proceedings of the Second Annual International Symposium on Medical Robotics and Computer Assisted Surgery*, Baltimore, MD; 11/4–7/95.

Finlay; Orthosista™ An Active Surgical Localiser for Assisting Orthopaedic Fracture Fixation; *Proceedings of the Second Annual International Symposium on Medical Robotics and Computer Assisted Surgery*; Baltimore, MD; 11/4–7/95.

Visarius, et al.; Man–Machine Interfaces in Computer Assisted Surgery; *Proceedings of the Second Annual International Symposium on Medical Robotics and Computer Assisted Surgery*; Baltimore, MD; 11/4–7/95.

Phillips, et al.; Image Guided Orthopaedic Surgery Design and Analysis; *IEEE Transactions on Robotics and Control*; 3/96.

Hofstetter, et al.; Fluoroscopy Based Surgical Navigation— Concept and Clinical Applications; *Proceedings of the 11$^{th}$ International Symposium and Exhibition on Computer Assisted Radiology and Surgery*; Berlin; 6/25–28/97.

Joskowicz, et al.; Computer–Aided Image–Guided Bone Fracture Surgery; Concept and Implementation; *Proceedings of the 12$^{th}$ Computer Assisted Radiology and Surgery Symposium*; Tokyo; 1998.

* cited by examiner

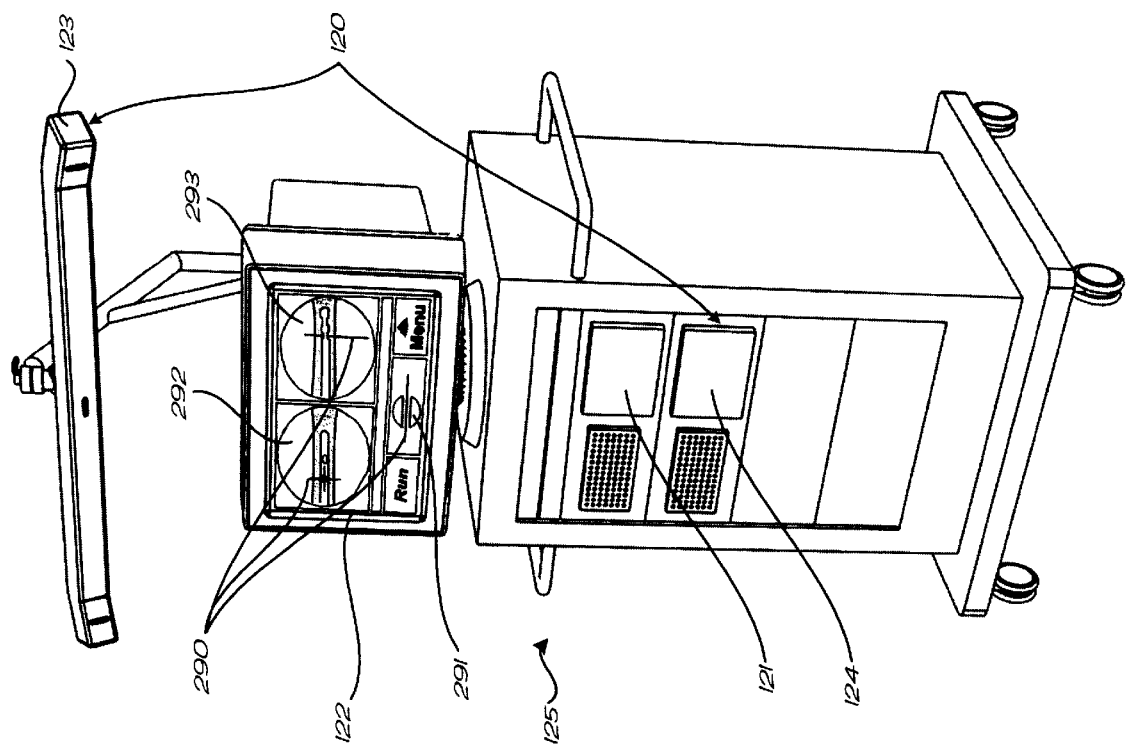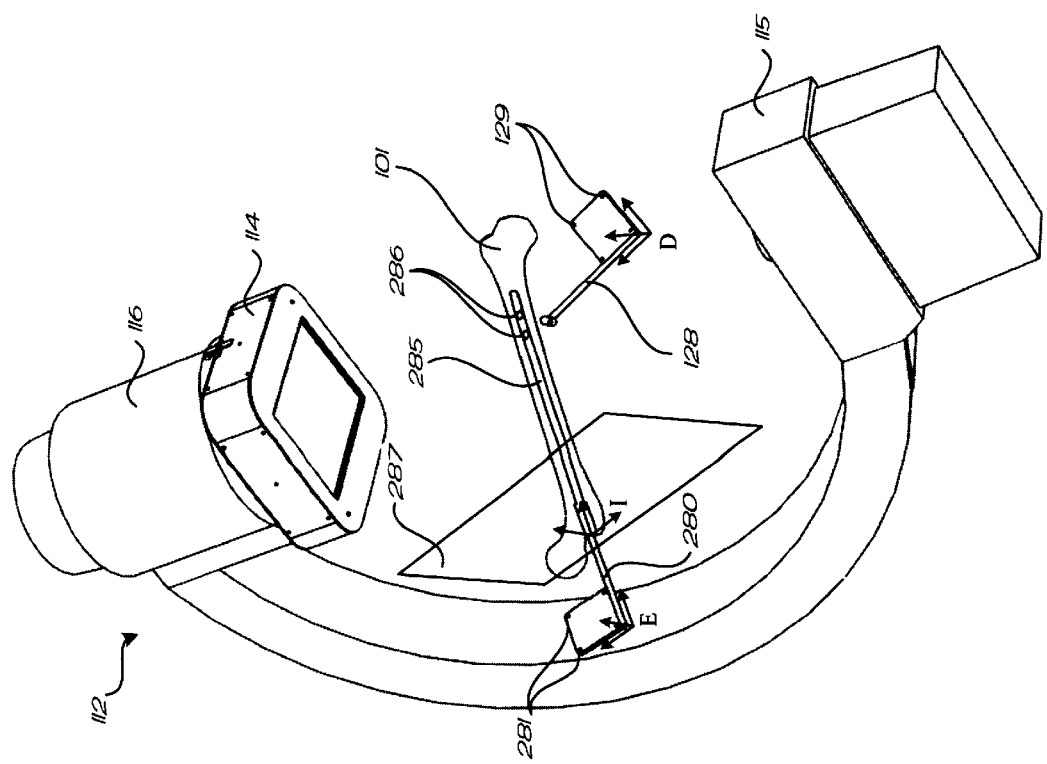
Fig. 18

COMPUTER ASSISTED TARGETING DEVICE FOR USE IN ORTHOPAEDIC SURGERY

GRANT REFERENCE

This invention was made with government support under SBIR grant 1 R43 AR44759-01 awarded by the National Institutes of Health. The government has certain rights in the invention.

BACKGROUND OF THE INVENTION

1. Field of the Invention

This invention relates to a system for use in computer assisted surgery. More specifically, the invention relates to a system for providing visual feedback regarding surgical tool positioning with respect to fluoroscopic images of a body part during an orthopaedic procedure.

The invention also relates to a system for providing the surgeon with improved visual feedback for the positioning of one surgical tool with respect to another surgical tool or implant.

2. Description of the Related Art

Orthopaedic procedures generally involve the fixation of a screw, plate, prosthetic component, or other implant to the bone of a patient. Typically the bone into which the implant is inserted or affixed is only partially exposed to the surgeon's vision. In order to align the implant with respect to the unexposed bone, some sort of imaging modality is required (preoperative x-rays, preoperative CT scans, or intraoperative x-rays using a C-arm fluoroscope). However, these images can be very difficult to correlate to the patient's anatomy in a useful manner. The field of image guided surgery is concerned with the use of computer technology to present these images to the surgeon in a manner that makes them more relevant and useful.

In the case of intertrochanteric hip fractures, the treatment of choice is the insertion of a lag compression screw. The first step in this procedure is the insertion of a guide pin along the intended trajectory of the screw from the lateral femur through the center the femoral head. This has been traditionally performed with repeated images from a C-arm, allowing the surgeon to monitor the alignment and progress of the guide pin insertion. Because x-ray images provide information in only two dimensions, two separate images taken from different positions are required to demonstrate the correct positioning of the guide pin in three dimensions. In practice, this means that the C-arm must be repositioned each time an updated set of images is acquired. Not only does this add to the duration of surgery, but during this time the surgical instrument visible in the existing image may move. Thus it is not guaranteed that two orthogonal images will represent the current pose of the surgical tool. (An object's pose may be defined as its position in space and, to the extent known or calculable, its orientation.) Further, the images that are acquired by the C-arm do not represent linear projections of the anatomy. The image captured by the image intensifier and camera unit of the C-arm is subject to distortions due to both the geometry of the image intensifier and the effect of magnetic fields (including Earth's magnetic field) on its internal electron beam. These cause a "warping" of the image and lead to straight objects appearing curved in the x-ray images. Further, the degree of distortion varies with respect to several factors including C-arm orientation, image intensifier shielding and size and proximity of ferrous objects. Other factors, such as rigidity of the source/receiver connecting structure and operating temperature, as well as magnetic fields, induce a translational offset to the image.

This inability to obtain accurate and linear images, simultaneously in two views, may lead the surgeon to insert the guide pin along a path other than the intended one. These misplaced attempts can add significantly to the duration of the surgery and the amount of radiation exposure to OR personnel as well as compromise of the bone stock. Further, the risks of a prolonged procedure and the difficulty of inserting a guide pin near the hole from a previous failed attempt may lead the surgeon to accept a pin position that is suboptimal. A serious complication, the "cutting out" of the screw through the femoral head into the hip joint, has been linked in numerous studies to poor placement of the screw.

Several image guided systems have been proposed to deal with the problems of this and similar surgeries. U.S. Pat No. 5,517,990, Kalfas, et. al., May 21, 1996, describes an image guided surgical system that is similar in concept to the majority of systems currently in use. This system uses sonic tracking of a probe to navigate CT data of the patient's head or spine. However, CT scans are not indicated for most orthopaedic trauma procedures and would add significantly to the cost of treatment if obtained. Further, CT scans must be registered to the bony anatomy (i.e., a mathematical relationship must be found between the coordinate frames of the CT scan and of the bone). This requires an intraoperative step in which a probe is used to sample the positions of landmarks on the bone as these same points are selected in the imaging data. (Alternatively, small radiopaque markers may be used as landmarks.) Such systems and their complicated user interfaces are often found by surgeons to be time consuming and difficult to use.

Another image guided system has been described in U.S. Pat. No. 5,772,594, Barrick, Jun. 30, 1998. This system displays the pose of a surgical tool over intraoperative fluoroscopic images during hip screw placement. This system, however, requires that the bone be registered to the images by finding small, different shaped, radiopaque markers. This introduces extra steps to the process and may negate the potential time savings. Also, no method is described for the correction of the nonlinearities present in the C-arm images.

Another solution for the difficulties in hip screw placement is proposed by Phillips, et. al. They describe a fluoroscopic system wherein image processing techniques are used to identify a path for the guide pin. The surgeon then implements this by aligning the tool, connected to a passive manipulator, until crosshairs on the display align. The drawback of this system is that it uses the surgeon as an assistant to implement its plan instead of providing improved information to the surgeon with which to plan and execute the procedure.

Another application for the system proposed by Phillips, et. al. is the insertion of a screw through a transverse hole in the distal end of an intramedullary (IM) rod that has been inserted down the central canal of a fractured femur. In order to insert this locking screw, a hole is drilled in the bone exactly at the location of the transverse hole with the same orientation. Currently the surgeon aligns the C-arm with the transverse holes so that they appear as "perfect circles" in the images. The surgeon then uses repeated images to align the tip of the drill with the center of the hole while using the C-arm source and receiver as external reference points to correctly orient the drill. This procedure involves numerous x-ray images and often requires several attempts before the screw hole is acceptably placed.

The biggest drawback with using a C-arm to position a drill for IM rod screw insertion is the difficulty encountered in achieving the accurate orientation of the drill in the axial plane. External jigs, attached to the exposed proximal end of the IM rod, have been proposed to assist in the placement of the distal screw holes, but these are unable to account for flex of the IM rod in the bone and therefore are not very useful. The system proposed by Phillips, et. al. extracts features from fluoroscopic images of the inserted IM rod and uses image processing techniques to calculate the trajectory required to pass a drill through the hole. The surgeon then moves a drill guide attached to a passive manipulator until the proper position is achieved and then drills the hole. Again, the drawback of this system is that it uses the surgeon as an assistant in implementing its plan instead of providing improved information to the surgeon with which to plan and execute the procedure.

A similar difficulty encountered by surgeons is the accurate placement of a hole or guide pin through an irregularly shaped or partially obscured bone when fluoroscopic guidance is not used. For example, when drilling holes through the patella for tendon or fracture repairs or the calcaneous for fracture fixation, it may be difficult to correctly align the drill with the intended exit point. The system described in U.S. Pat. No. 5,305,203, Raab, Apr. 19, 1994, includes a means for implementing a previously specified drill trajectory as part of a menu driven surgical system. A drawback of this system is the sequential nature of the indication of the entry point, the indication of the exit point and the implementation of the trajectory by a single passive manipulator arm.

Many of these systems often suffer from a lack of readiness for the operating room. As academic or conceptual systems they do not always address practical considerations. Many systems introduce extra equipment and operative steps to the surgical procedures that prolong the surgery and require significant training. Further, most of the systems do not address the issues of sterility, error checking and safety, and unwanted motion of the body part to be operated upon.

Most systems require input from the surgeon in order to specify data or alter program flow. Many systems rely on a non-sterile assistant to enter data at a keyboard or with a mouse, but this is inefficient and risks miscommunication. A sterilized or draped input device introduced into the surgical field may be difficult to use and distracting for the surgeon. Visarius describes an input scheme in which the surgeon points to fields on a tracked, sterile "virtual keyboard" with the surgical tool. The input scheme described in U.S. Pat. No. 5,230,623, Guthrie, Jul. 27, 1993 uses the surgical tool pointing to an area in space to move a mouse cursor on the screen via an "imaginary mathematical correspondence". Both, however, require the splitting of the surgeon's attention between the display screen in one location and the surgical tool in another as well as the removal of the tool from the surgical site for use elsewhere as an input device.

In order that any motion of the body part which is being operated upon not affect the accurate superposition of the tool on the image data, many systems use a dynamic reference frame. U.S. Pat. No. 5,383,454, Bucholz, Jan. 24, 1995, describes the measurement of all surgical tool poses relative to a ring or to markers attached to the patient's head. This allows the registration between the three dimensional image data and the patient's skull, as well as the accurate positioning of the tool relative to the head, to be maintained despite motion of the head. However, some surgeries, especially orthopaedic trauma procedures, involve multiple body parts (e.g., bone fragments, soft tissue). While not freely mobile, these untracked body parts may experience significant motion if associated structures are moved excessively.

SUMMARY OF THE INVENTION

Accordingly one feature of our invention is an image guided surgical system that provides a surgeon with improved visualization of the relationship between surgical tools and the involved body part, by accurately superimposing representations of tools being used in the surgical field over the images of the body part such that real-time tool position feedback is provided to the surgeon, and which comprises a controller, display device, localizing device, and surgical tools with localizing emitters and which receives image data from a fluoroscopic x-ray device, preferably a C-arm.

A related feature of the invention is the use of a fluoroscopic x-ray device employing a digital flat-panel x-ray imager comprised of a regular array of sensors to convert incident x-ray energy to a computer readable image, and has the advantage of improving the accuracy with which the imaging chain can be modeled and permits the fluoroscopic x-ray device to be used in any orientation without being affected by distortions due to local magnetic fields.

Another feature of the invention is the preoperative determination of imaging model parameters, including conic projection parameters and mapping parameters, that closely model the imaging chain of the x-ray device, and are determined by a process employing a radiopaque calibration grid placed between the x-ray source and x-ray receiver.

A related feature of the invention is the determination of the conic projection model parameters for a plurality of orientations of the fluoroscopic x-ray device.

Another feature of the invention is the specification of a conic projection model, including its pose, and the calculation of conic projection parameters through interpolation of preoperatively determined pose-specific calibration data, said conic projection model simulating the way an acquired image is formed on the fluoroscopic x-ray device's input surface during surgery, such that points in space can be mapped to image space in an accurate simulation of the imaging chain of the fluoroscopic device, and has the advantage of permitting accurate superposition of graphic representations of surgical objects on fluoroscopic images of a body part without the requirement for registration of the body part itself.

Another feature of the invention is a surgical tool outfitted with a plurality of localizing emitters such that its pose can be continuously measured by a localizing device, and that has an associated three dimensional graphics model, such that points comprising the model can be assigned a position in space, transformed into image space using the conic projection model and mapping equations corresponding to an acquired image, and then superimposed on that image, thereby producing a graphic representation of the surgical tool that duplicates the movement of the tool in real time.

Another feature of the invention is a device outfitted with a plurality of localizing emitters such that its pose can be continuously measured by a localizing device, and that relatively small translational and rotational motions of the body part to which the device is attached can be determined and a compensatory adjustment made to the tool representation on the image to preserve the accurate relationship between the tool representation and the image of the body part, while larger motions raise a warning to the surgeon.

Still another feature of the invention is software that assists the surgeon in verifying the accurate superposition of a representation of a tool over an x-ray image of that tool whose pose is recorded at the time of image acquisition and which is generated in the same manner as the real-time representation, but is retained on the screen until the surgeon has had time to visually determine its accurate superposition over the silhouette of the surgical tool in the x-ray image.

Still another feature of the invention is software that provides a direct and convenient user interface by performing specified actions when the intersection of the trajectory of the surgical tool with the plane of the display device screen occurs in specified screen fields and an activation criterion, such as continued field selection or the press of a button, is satisfied.

Still another feature of the invention is a sterile transparent drape that allows the C-arm to be used in a sterile environment, and that includes a portion similar in size and shape to the housing that contains the C-arm localizing emitters, such that the drape fits flat and flush against the localizing emitters, so that their positions may be accurately determined by a localizing device.

A feature of an alternative embodiment is a plurality of localizing device sensor units that permit the localization of emitters on either side of an obstruction such as a sterile drape, and can further be reoriented to provide a wider field of view or a more accurate, redundant, narrower field of view, and that further comprises controller software to coordinate the activation of localizer sensor units and localizing emitters and to select the appropriate position data from the multiple localizer sensor units to calculate the most accurate emitter location, and that further comprises a registration object containing localizing emitters and a registration procedure for determining the pose of one localizing device sensor relative to another.

A feature of an alternative embodiment is a computer assisted surgical system that assists a surgeon in positioning a first surgical tool with respect to a second surgical tool by providing a continuously updated picture of the relative poses of the two tools, and which further provides for the software selection of the projection method and plane that generates this picture, and which comprises a controller, display device, localizing device, and surgical tools with localizing emitters.

A feature of an alternative embodiment is an image guided surgical system that assists the surgeon by providing information regarding the pose of a first surgical tool relative to images of a body part and relative to a second surgical tool, by accurately superimposing a representation of the first tool over the images of the body part such that real-time tool pose feedback is provided to the surgeon, and by providing a continuously updated picture of the relative poses of the two tools, and which further provides for the software selection of the projection method and plane that generates this picture, said system comprising a controller, display device, localizing device, and two surgical tools with localizing emitters and which receives image data from a fluoroscopic x-ray device, preferably a C-arm.

These and other features and advantages are, in the present invention, embodied in an improved system for assisting a surgeon in positioning a surgical tool, optionally connected to an implant, with respect to a body part. The system uses a one-time calibration process involving a calibration grid, containing markers visible in x-ray images, to determine pose specific imaging model parameters which are stored in the controller. As images are acquired during surgery, the pose of the fluoroscopic x-ray device containing localizing emitters is measured by a localizing device. Imaging model parameters are interpolated from the calibration data to simulate the fluoroscope's imaging chain for the pose at which the image was acquired. The poses of surgical tools, containing localizing emitters, are continuously measured by a localizing device. The points of a three dimensional graphic model representing the surgical tool in its pose, are transformed by the imaging model to develop a two dimensional graphic representation of the tool in image space that is superimposed on the corresponding x-ray image. The modeling of the fluoroscopic device for each acquired x-ray image has the advantage of permitting the accurate projection of surgical tool representations on fluoroscopic images of a body part without the requirement for registration of the body part itself.

An feature of the system is the use of a digital flat-panel x-ray imaging device as the source of x-ray images. Such a device provides, for a wide range of operating conditions, high spatial linearity between the x-ray pattern striking its input surface and the resultant electronic image generated. The use of a digital x-ray imager in an image guided system allows for simplified and accurate modeling of the imaging chain. Such a system, which includes surgical tools tracked by a localizing device, is able to provide accurate real-time feedback to the surgeon of the tool poses relative to the involved anatomy.

Other aspects of the invention relate to its reliability and ease of use. A software feature causes the persistence of the representation of a surgical tool on the screen in its pose at the time an image was acquired. This allows the surgeon to verify the system's accuracy by comparing the superimposed tool representation to the actual x-ray image of the tool. The means for providing the surgeon with time to determine the accuracy of the system may be a timer of predetermined value or the surgeon may control this feature via a button press, a keyboard command, or even a specific tool motion.

Another software feature, intended to provide the surgeon with an interface to the system, calculates the location of the intersection of the surgical tool's trajectory with the plane of the display screen. If this intersection falls within previously defined areas of the screen, and an activation criteria is satisfied (such as continued selection for a specified period of time), an associated software action is performed.

Another feature is the use of multiple localizing device sensor units to determine pose data of surgical objects either in a wide field of view, more accurately in a narrow field of view, or when the field of view of a single sensor is obstructed, as by a surgical drape.

Another aspect of the invention is the use of the system without imaging data to assist the surgeon in positioning one surgical tool with respect to another. A first surgical tool, containing localizing emitters, is held in a pose with respect to the body part. A second surgical tool, also containing localizing emitters, is held relative to the first surgical tool. A localizing device determines the poses of both tools. A picture plane is chosen in space, and representations of one or more tools are projected onto the picture plane. The surgeon then orients the surgical tools based on the continuous feedback of their representations on the display screen.

Still another aspect of the invention is the use of the system simultaneously both with a representation of a surgical tool superimposed on x-ray imaging data, and in a picture showing the relationship to a representation of a second tool.

BRIEF DESCRIPTION OF THE DRAWINGS

FIG. 18 is a perspective view of a surgical tool attached to an intramedullary rod inside a femur, the drill guide, a partial C-arm with attached flat panel imager, and the system cart with optical localizer, controllers and monitor screen containing images and graphics.

DETAILED DESCRIPTION OF THE INVENTION

Figure 1:
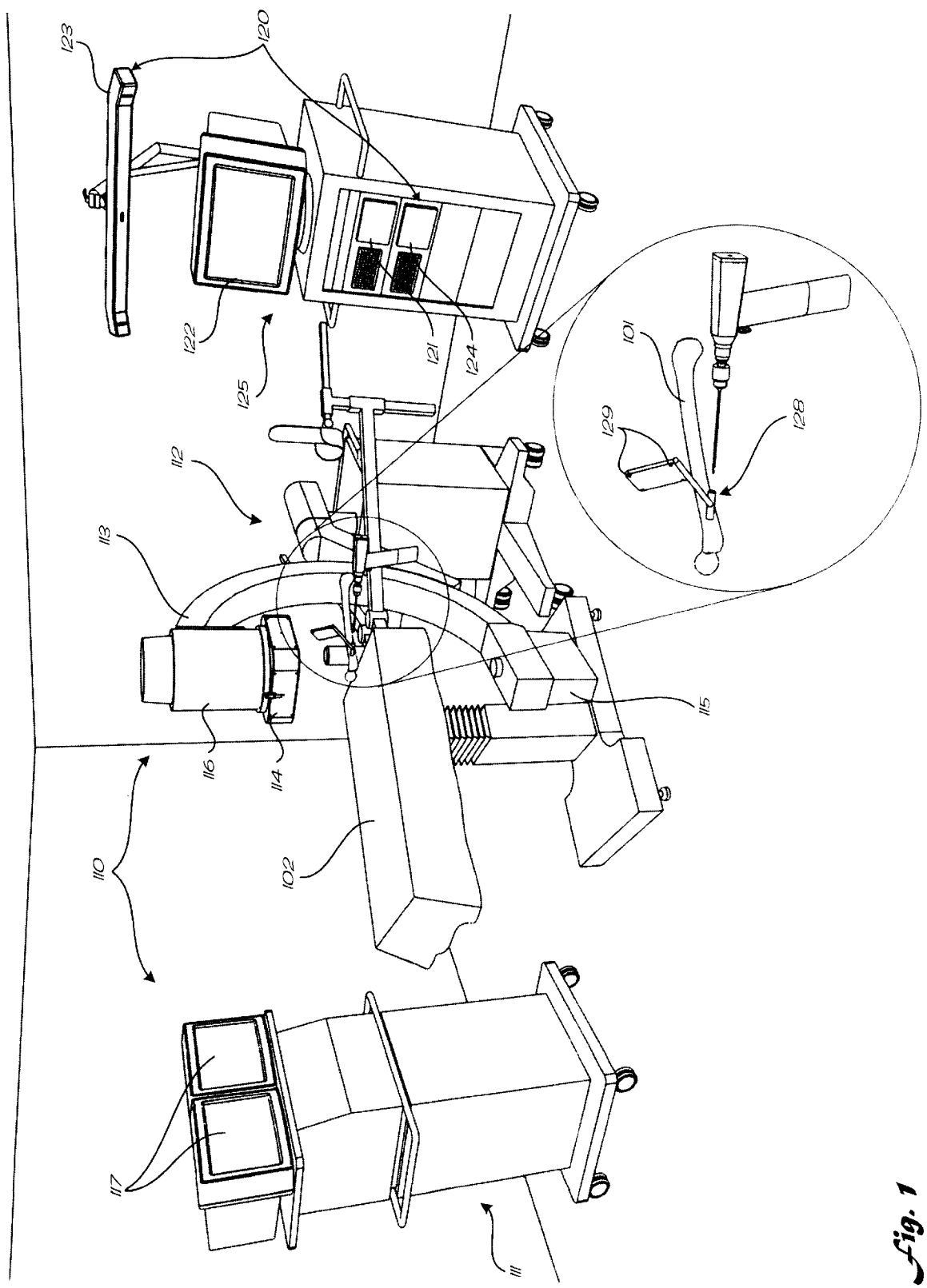
FIG. 1 is a perspective view of an operating room outfitted for surgery using the invention.

In the preferred embodiment, the invention is intended for use in an operating room during an orthopaedic surgical procedure. Generally, with respect to FIG. 1, the patient is placed on a standard surgical table 102 so as to provide access to the body part 101 to be operated upon. A mobile fluoroscopic x-ray imaging device 110 with a flat panel x-ray imager 114 is used to obtain multiple images of the patient's bony anatomy 101. Although not required, the images typically are taken in near orthogonal views. The images are then supplied to the system controller 121. A surgical tool 128 containing a plurality of localizing emitters 129 is used in the performance of the surgical procedure. The localizing emitters 129 are viewable by a localizing device 120 that reports the pose of the surgical tool 128 to the system controller 121. The system controller 121 then displays on the system monitor 122 the images of the patient's anatomy superimposed with representations of the surgical tool 128 at its current pose. As the surgical tool 128 is moved relative to the patient's bone 101, the superimposed tool representations are updated continuously on the system monitor 122, providing real-time visual feedback to the surgeon during the performance of the surgical procedure.

System Architecture

In the preferred embodiment, the invention is intended for use in the operating room with a mobile fluoroscopic imaging device 110, such as what is commonly referred to as a C-arm. (The term "fluoroscopic" here refers to the ability of an x-ray device to rapidly convert x-rays into an electronic image; it is not necessary that the x-ray device be able to do this several times per second in order to simulate "live" images.) This standard piece of operating room equipment has an x-ray source 115 and an x-ray receiver 116 attached to either end of a "C" shaped beam 113. The x-ray receiver 116 typically comprises an image intensifier tube (not shown) and a video camera (not shown). Adjustable links on the C-arm allow the "C" shaped beam 113 with the x-ray source 115 and x-ray receiver 116 to be oriented in a wide range of poses with respect to the patient's anatomy 101. These adjustments to the x-ray source 115 and receiver 116 include rotation about a horizontal axis parallel to the long axis of the C-arm 112 (C-arm rotation), or about a horizontal axis perpendicular to the C-arm 112 (C-arm inclination). The C-arm 112 further comprises mechanical and electrical devices for controlling the generation of the x-ray beam and its conversion into an image signal. These functions include, but are not limited to, the supply and control of high voltage electricity to the x-ray tube, collimation of the x-ray beam, elevation of the source and receiver, and rotation and reversal of the acquired image.

An auxiliary part of the C-arm 110, the monitor cart 111, typically comprises an imaging controller (not shown) and one or two display monitors 117. The imaging controller and display monitors 117 control the processing, manipulation, storage, retrieval, and display of the images acquired from the x-ray receiver 116.

Alternatively, any imaging device may supply the image data for the invention provided that the image data is in computer readable format and that the imaging chain of the imaging device may be mathematically modeled to sufficient accuracy. These alternative imaging devices may include other x-ray devices, video cameras, endoscopic cameras, ultrasound sensors, and other imaging modalities.

Figure 2:
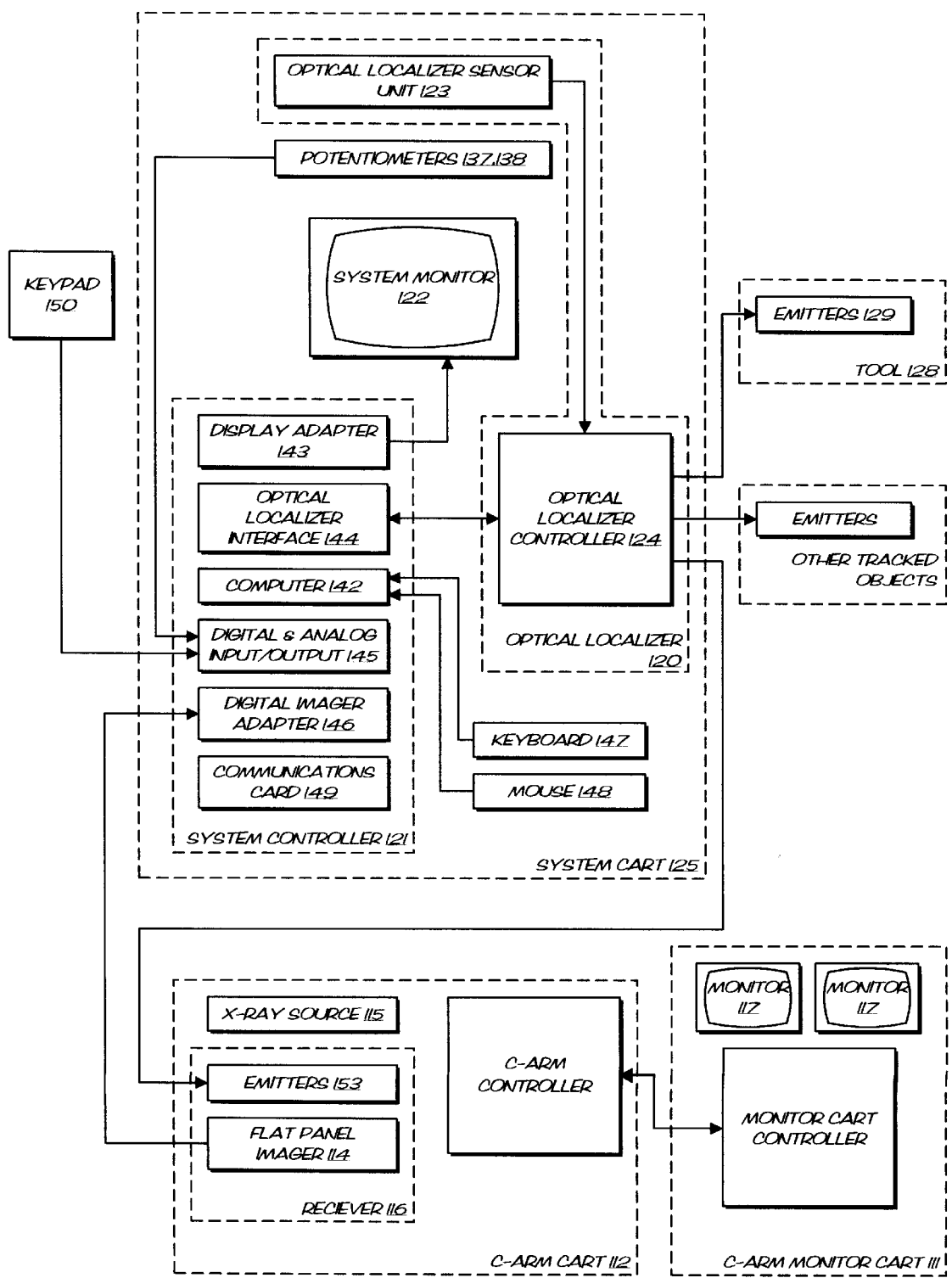
FIG. 2 is a block diagram of the invention and its interconnections to itself and a mobile fluoroscope device.

In the preferred embodiment, the invention comprises a mobile cart 125 housing several components, including a localizing device 120, a controller 121, and display device 122. Referring to FIG. 2 the controller 121, hereafter referred to as the system controller, preferably comprises a computer 142 based on a Pentium II processor with a display adapter 143, an optical localizer interface 144, digital/analog input/output card 145, and an interface card for acquisition of x-ray images 146. Alternatively, any computer of sufficient speed and capacity, including the C-arm controller, may assume the functions of the system controller. Additionally, a keyboard 147, mouse 148 and communications card 149 (such as an Ethernet card or modem) may be included for diagnostics or data entry. Connector ports on the cart 125 are provided for output to localizing emitters 129, input of the image signal, and input from a hand-held keypad 150 that permits remote control of the system.

In the preferred embodiment, the display device comprises a single wide-screen CRT monitor, hereafter referred to as the system monitor 122. Alternatively, the display device may comprise a flat panel display, multiple display monitors, or any other means for displaying the images and graphics to the surgeon. In an alternative embodiment, the display device may comprise the display monitors 117 of the fluoroscopic imaging device 110.

In the preferred embodiment, the localizing device 120 is an optical localizer comprising a sensor unit 123 and a controller unit 124. The controller unit 124 comprises a Pentium PC with software and specialized hardware to sequentially activate localizing emitters 129 and to convert the resulting data from the sensor unit 123 into location data. The sensor unit 123 comprises three cylindrical lenses focusing on separate linear charged couple device (CCD) sensor elements sensitive to infrared light. When an emitter 129, preferably an infrared light emitting diode, is in the field of view of the sensor unit 123, the localizer controller 124 analyzes the three sensor element images and determines the emitter's position in space. If three or more LEDs 129 are placed non-collinearly on a single tool 128 and a description of their relative positions is provided to the localizer controller 124, the localizer controller 124 can calculate the tool's pose. One suitable optical localizer is the Flashpoint Model 5000 manufactured by Image Guided Technologies, Inc. of Boulder, Colo.

Alternatively, the localizing device 120 can comprise an electromagnetic or radio frequency triangulation system, a visible light sensor system, an infrared system with two 2D sensor units, or one or more passive manipulators. Further, the localizing device may comprise a sensor unit for reading the positions of energy reflectors placed on the objects to be tracked or may comprise sensors attached to the surgical tools for the purpose of determining their poses. In these cases, the reflectors and sensors are analogous to the localizing emitters and the energy source/sensor unit and energy source, respectively, are analogous to the localizer sensor unit. Any localizing device may be used that is capable of determining an object's pose without departing from the scope of the instant invention.

Figure 3:
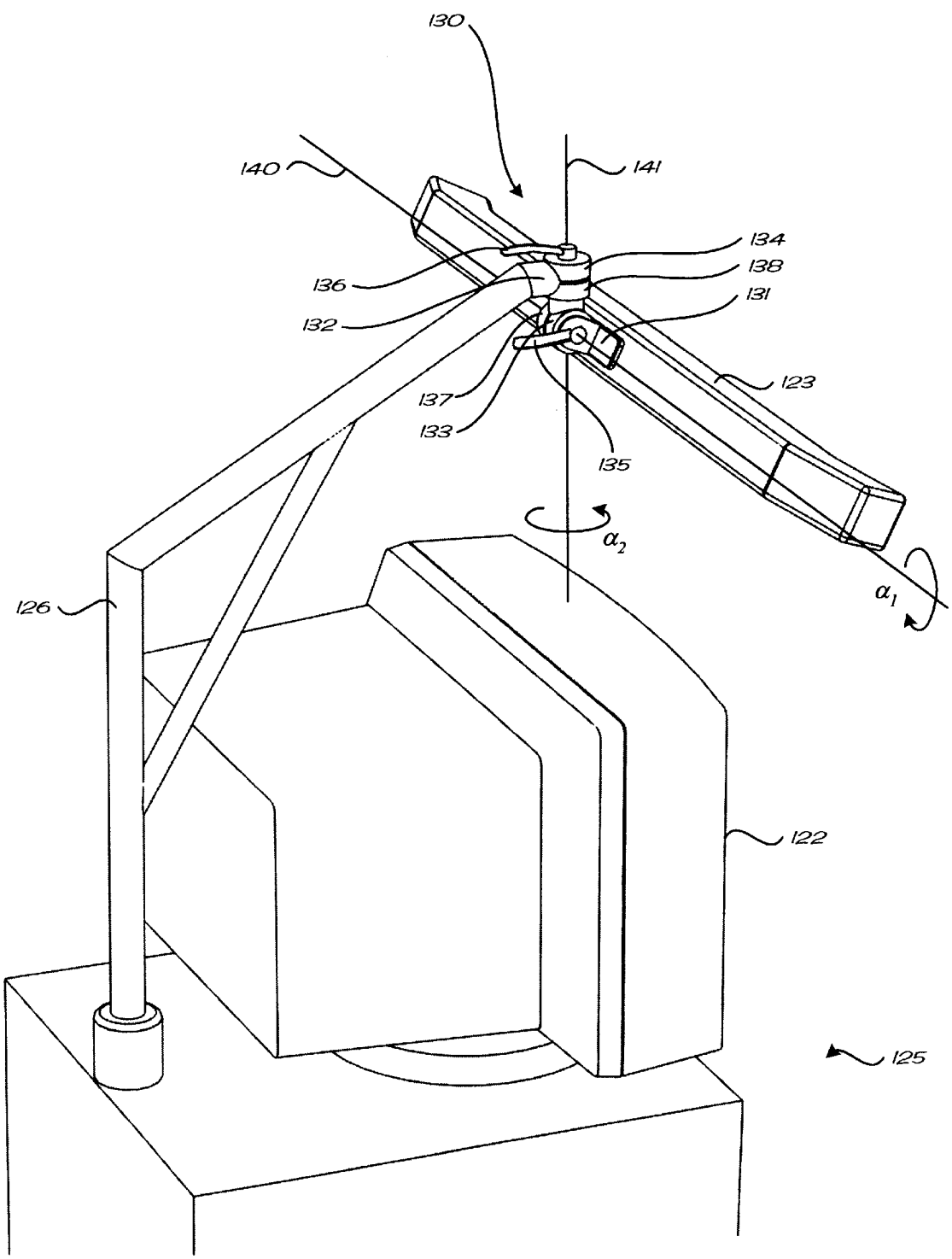
FIG. 3 is a detail perspective view of the optical localizer sensor unit, its support structure and mounting means and partial system cart.

Turning to FIG. 3, the support structure for the sensor unit 123 of the localizing device 120 preferably comprises the cart 125 and an attached rigid support arm 126 terminating in the sensor unit mounting means 130. The mounting means 130 comprises an attachment point 131 for the sensor unit 123 and an attachment point 132 for the support arm 126 separated by two pivoting joints 133, 134. Rotation at the first joint 133 results in inclination of the sensor unit 123 about the horizontal axis 140. The second joint 134 is oriented at a right angle to the first and rotation about it results in pivoting of the sensor unit 123 about a vertical axis 141. Each joint includes locking mechanisms 135, 136 and potentiometers 137, 138 whose positions change as the joints 133, 134 are rotated. The potentiometers 137, 138 are connected in voltage divider configurations so as to provide unique voltage output for all possible joint positions. Alternatively, any suitable rotary position sensor and reporting scheme may be used.

Subsequent to assembly, a calibration routine is performed to determine the relationships between the angular positions, $\alpha_1$ and $\alpha_2$, of the joints 133, 134 and the output voltage $v_1$ and $v_2$ of the potentiometers 137, 138. Preferably, each joint is taken through its maximum anticipated range of motion in 5° increments as measured by an external protractor while the resulting potentiometer output voltage is recorded. Preferably, the zero position for the joints 133, 134 are those which result in the sensor unit 123 facing horizontally and directly forward relative to the system cart 125. For example, the maximum anticipated range of motion for the sensor unit 123 might be 0° to 90° (straight down) inclination and ±45° side-to-side rotation. The two sets of angles and corresponding potentiometer voltages are stored in the system controller's long term memory for later use as look-up tables.

In an alternative embodiment, two or more optical localizer sensor units may be used. The additional units each have mounting means that provide for inclination about a horizontal axis and rotation about a vertical axis. Each degree of freedom has a separate joint with a locking mechanism and the inclination joint has a potentiometer or other rotary position sensor.

Alternatively, the localizer sensor elements may be mounted, individually or in groups of sensor units, in a permanent or adjustable fashion to other mounting means. These other mounting means may include tripods, operating room light supports, or the operating room wall or ceiling. Any supporting means may be employed that holds the localizer sensors with sufficient rigidity and in a pose that allows them to view the objects to be tracked.

Figure 4:
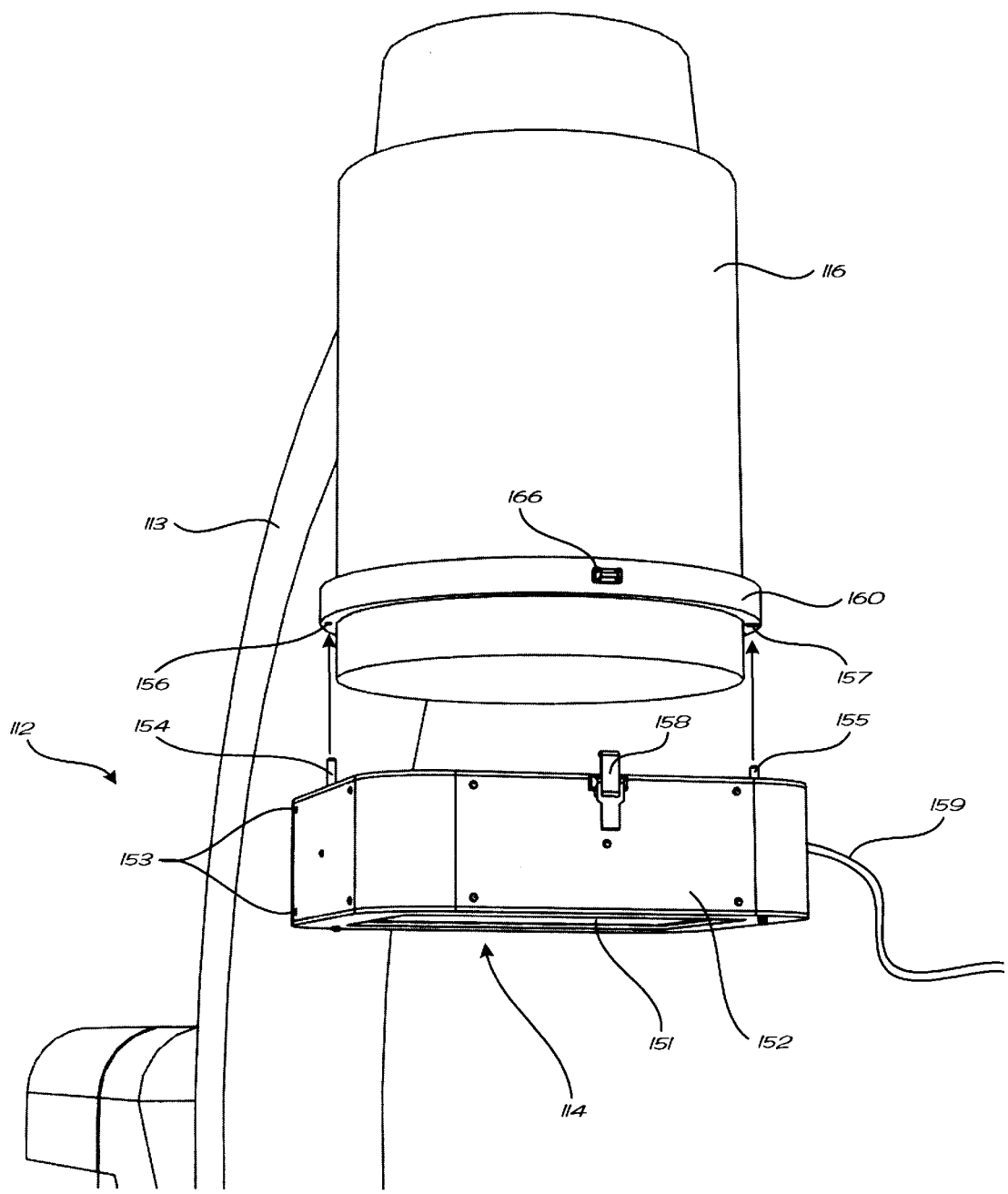
FIG. 4 is a perspective view of a C-arm receiver unit modified with a mounting ring and the digital flat panel x-ray imager and housing assembly to which it mates.

In the preferred embodiment, seen in FIG. 4, the x-ray imager 114 is a flat panel x-ray imager 151 mounted in a housing 152 that also contains localizing emitters 153, and can be repeatably mounted on the receiver end 116 of the C-arm 112 where the x-ray beam strikes it. The digital flat panel x-ray imager 151 comprises a highly regular array of semiconductor sensing elements that produce an electric signal in response to incident x-ray energy. These individual signals are read out, typically in a serial fashion, to produce a combined signal representing the x-ray image. By using an imaging device based on a flat and highly regular array of sensors, spatial linearity is preserved in the resulting image. The images so produced are also free of distortion from magnetic fields (including those of Earth and due to nearby ferrous objects). These factors allow for extremely accurate mathematical mappings from the physical surface of the imager 114 to the resultant image space which permits the accurate mapping of a surgical tool representation into image space from points projected on the surface of the imaging device 114. The inclusion of the flat panel x-ray imager 151 in this invention thus represents a significant improvement over existing fluoroscopic image guided systems as it permits the accurate and reliable correlation of a surgical tool 128 with the acquired image.

In an alternative embodiment, the image signal is derived from a C-arm's image intensifier. In this case, corrective techniques can be used to minimize distortions imposed by the Earth's and local magnetic fields. These include magnetic shielding of the image intensifier and mathematical modeling of the effects due to the image intensifier's geometry and due to Earth's magnetic field.

In the preferred embodiment, three or more localizing emitters 153 are affixed to the flat panel imager housing 152 in a non-collinear fashion. Further, a cable 159 or other transmission means is employed to transfer the image signal from the flat panel imager 151 to the system controller 121 and to transfer strobing signals from the localizer controller 124 to the localizing emitters 153. The housing 152 is manufactured such that it may be removed and repeatably reattached to the same position on the receiver end 116 of the C-arm 112. A mounting ring 160 is rigidly attached to the C-arm receiver 116. Located on the mounting ring 160 are a hole 156 and a slot 157. The housing 152 for the flat panel x-ray imager 151 contains a peg 154 that mates into the mounting ring hole 156 and another peg 155 of different diameter that mates into the mounting ring slot 157. Two locking latches 158 on opposite sides of the x-ray imager housing 152 mate into notches 166 in the mounting ring 160. The pegs 154, 155 and latches 158 are of such precision as to prevent the imager housing 152 from attaching to the ring 160 unless all mating surfaces are correctly aligned and relatively free of foreign matter, thus ensuring a proper and repeatable fit. Other mounting means that provide a rigid and repeatable attachment of the imager housing to the C-arm may be used without departing from the instant invention.

In an alternative embodiment, the flat panel x-ray imager 151 is integral to the C-arm 112. Localizing emitters 153 may be integral to the C-arm 112, being contained in the housing for the x-ray source 115, or in the housing for the x-ray receiver 116, or in both. Alternatively these localizing emitters may be contained in a housing (not shown) separate from the C-arm housing that may be attached to the exterior of the C-arm receiver 116 or x-ray source 115. Cables for connecting the system controller 121 to the flat panel 151 and the optical localizer controller 124 to the localizing emitters may be internal or external to the C-arm 112.

Mathematical Modeling of the Imaging Chain

In accordance with the invention, FIG. 1, a mathematical model of the imaging chain is developed. In the preferred embodiment, this imaging model includes the projection of points representing the surgical tool 128 onto the x-ray imager 114 by a conic projection model and the mapping of the projected points onto the system monitor display screen 122 by a mapping model. This permits representations of the surgical tool 128 to be accurately projected into a 2D representation and overlaid on the images of the body part 101. The development of these models requires that data regarding the C-arm 112 and the x-ray imager 114 be collected during a one-time calibration procedure. This procedure is preferably performed with an optical localizer and system controller. Preferably these are the same localizer and controller used during surgery, however, separate devices may be used.

Figure 5:
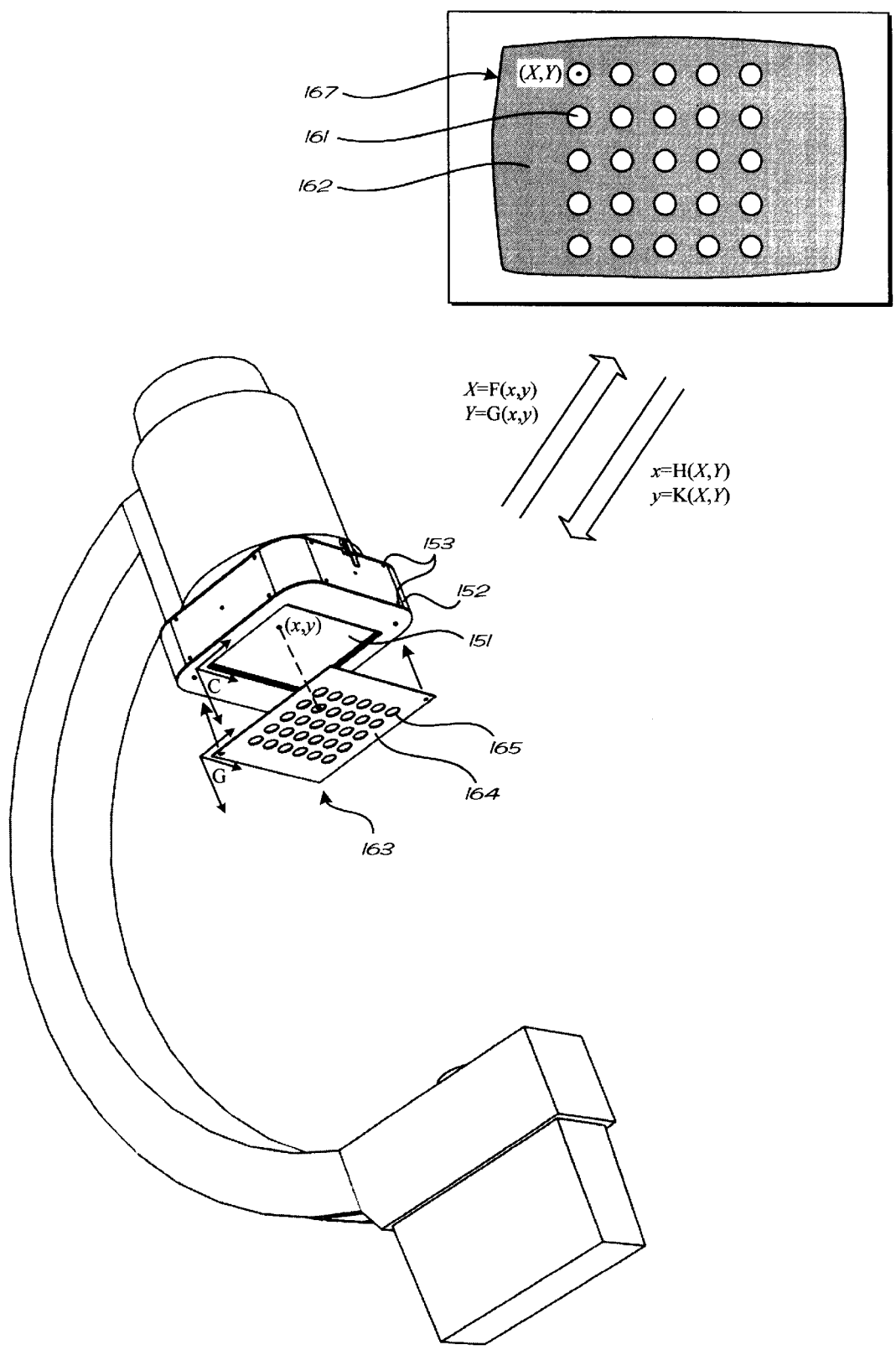
FIG. 5 is a perspective view of a partial C-arm with attached flat panel imager and a calibration grid, and a screen image of the grid pattern.

In the preferred embodiment, as seen in FIG. 5, mapping functions must be established between points on the input plane (i.e., the input surface of the x-ray imager 114) and their corresponding pixel locations in the acquired image. Parameters for these functions are specific for each flat panel imager 151 and housing assembly 152 and need to be determined only once. A coordinate frame, C, is assigned to an arbitrary point on the image plane and the locations of the localizing emitters 153 relative to this frame, contained in the x-ray imager housing 152, are known from manufacture within precise tolerances. Alternatively, the grid dimensions can be measured after its manufacture. The mapping function parameters, $X_{offset}$, $Y_{offset}$ and $\theta$, allow for the mathematical alignment of the flat panel imager 151 relative to coordinate frame C. This permits a point (x,y) on the image plane, measured relative to coordinate frame C, to be directly assigned to a specific pixel element (X,Y) of the flat panel imager 151 through use of the equations $$X = F(x,y) = \mu[(x - x_{offset})\cos\theta + (y - y_{offset})\sin\theta]$$

$$Y = G(x,y) = \mu[(y - y_{offset})\cos\theta - (x - x_{offset})\sin\theta]$$

where $x_{offset}$, $y_{offset}$ and $\theta$ represent translation and rotation parameters for the mapping functions and $\mu$ is a constant representing the linear density of sensor elements on the flat panel imager. The location of a point on the image plane corresponding to a specific screen pixel, is found with the inverse mapping functions $$x = H(X, Y) = \frac{1}{\mu}(X\cos\theta - Y\sin\theta) + x_{offset}$$

$$y = K(X, Y) = \frac{1}{\mu}(Y\cos\theta + X\sin\theta) + y_{offset}$$

Alternatively, F(x,y), G(x,y), H(X,Y), and K(X,Y) may take the form of interpolation functions whose values are derived from empirical data sets, or may be other suitable functions that provide accurate mappings between any point (x,y) on the image plane and a pixel location (X,Y) in the image.

In the preferred embodiment, the mapping function parameters are determined by a calibration process employing a grid 163, which preferably comprises a flat sheet of fairly radiopaque metal 164 with an array of radioparent circular holes 165 drilled in an evenly spaced rectangular pattern. The grid 163 can be clamped to the x-ray imager 114. Alternatively, the grid 163 may comprise a circuit board with an array of vertical and horizontal line traces, a sheet of polycarbonate (e.g., Lexan™) embedded with small steel balls, or any other suitable device with a set of markers of known positions in space which can be identified in the x-ray image.

The grid 163 is mounted on the input surface of the x-ray imager 114 such that the coordinate frame of the grid G is accurately known with respect to coordinate frame C. During the calibration process, an image of the grid 163 is acquired. The resulting grid image 167 is an array of light elliptical spots 161 on a dark background 162. The image is somewhat darker at the periphery due to the lower density of x-rays striking the border of the flat panel imager 151. An image of a similar flat sheet of metal without holes is subtracted from the grid image 167 to eliminate the brightness gradient present in the image, yielding a fairly uniform background illumination. A threshold value is established for the image and any pixel value below the threshold is set to zero (black). The image then contains small "islands" of pixel groups whose values are above the threshold and which are separated by a black "sea" of pixels set to zero. The center of each grid hole 161 in the image is then identified with sub-pixel accuracy by computation of its barycenter (center of mass).

Next, the locations of the centers of the actual grid holes 165 are calculated from the physical dimensions of the grid 163 as determined by the precision manufacturing process. Each of the physical hole locations (x, y) and the barycenters of its corresponding spot on the image (pixel location (X, Y)) is used to determine the mapping functions. Once values for all x, y, X, and Y are determined, a solution algorithm (such as singular value decomposition) can be used to find the parameters of the mapping equations and the inverse mapping equations. These mapping model parameters are then stored in the long term memory of the system controller 121.

Several alternate approaches to the calibration procedure are possible. The flat panel imager 151 and its housing 152 may be designed and manufactured such that the locations of the localizing emitters and imaging panel, and thus $x_{offset}$, $Y_{offset}$ and $\theta$, are known to sufficient precision. Alternatively, the calibration procedure could additionally determine the constant $\mu$, if the sensor element density is not known to sufficient precision or to determine $\mu_x$ and $\mu_y$ if there is a directional difference in the sensor element densities. Further, if it is determined that there is a significant variability of $\mu$, then mapping equations that take the form of a bivariate polynomial, interpolation functions based on empirical data sets, or some other form could be used to provide geometric accuracy over the whole flat panel.

Further, for situations where the mapping parameters change in response to variables such as the pose of the C-arm or operating temperature, multiple sets of mapping parameters can be acquired over the ranges of the variables and stored in the long term memory of the system controller. These data would then be available for later use to determine appropriate mapping model parameters for any arbitrary values of the variables.

Figure 6:
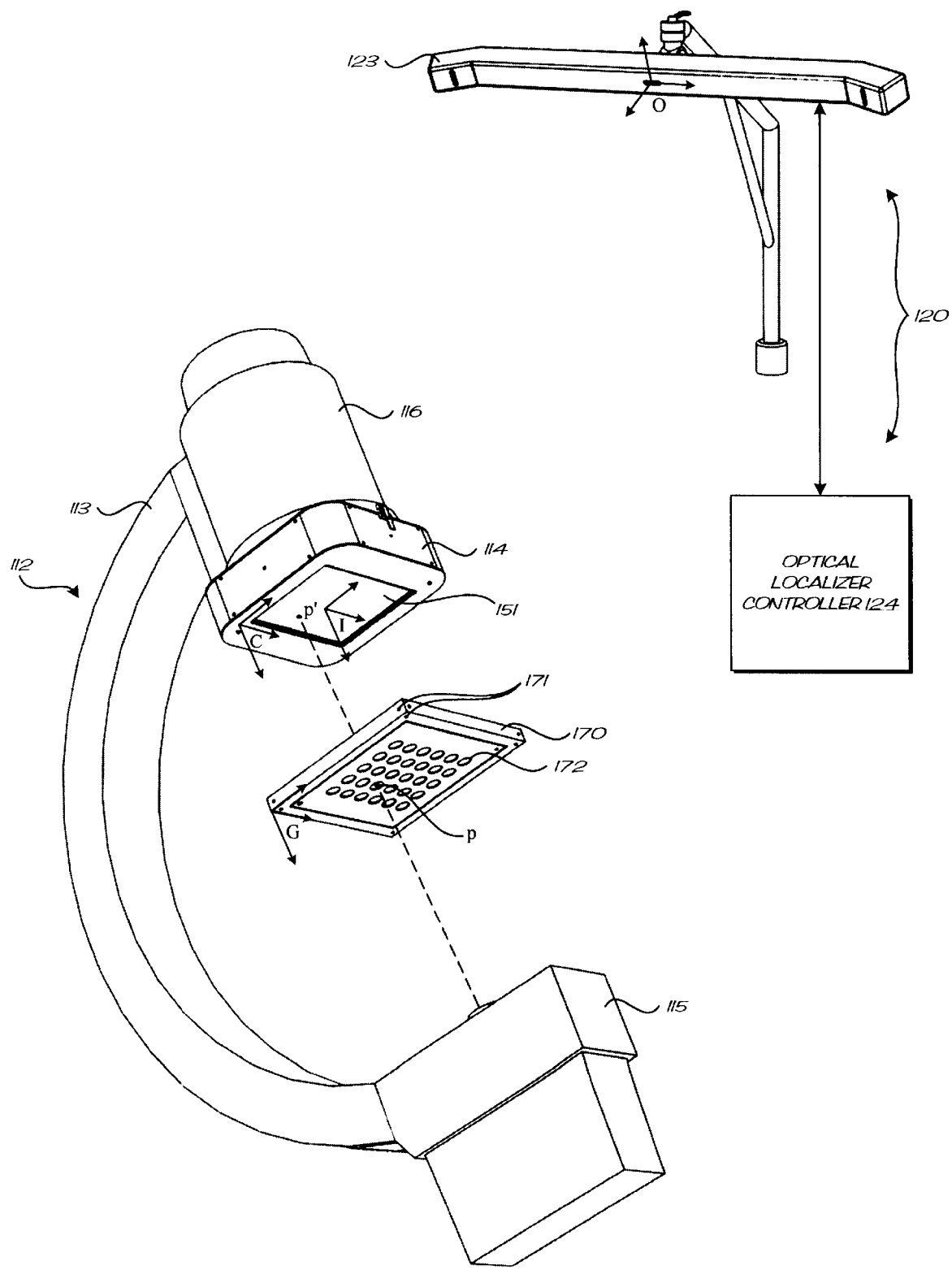
FIG. 6 is a perspective view of a partial C-arm with attached flat panel imager and a tracked calibration grid in view of an optical localizer sensor.

In the preferred embodiment, the mathematical simulation of the projection of points in space onto the image plane is accomplished by a conic projection model that involves three parameters. The determination of the parameters for the conic projection model is a one time procedure and the parameters are specific for each C-arm and C-arm pose. Referring to FIG. 6, a coordinate frame I is defined such that its x and y axes are contained in the image plane (the input surface of the flat panel imager 151) and have the same orientation as the x and y axes of coordinate frame C and so that its z axis passes through the x-ray source 115. Coordinate frame I is related to coordinate frame C by the transformation $^{C}T_I$. Since this transformation represents pure translation in the image plane, only two distance parameters, $t_x$ and $t_y$, need to be determined. The use of homogeneous transformations are well known in the art and $^{C}T_I$ is represented as $$^{C}T_I = \begin{bmatrix} 1 & 0 & 0 & t_x \\ 0 & 1 & 0 & t_y \\ 0 & 0 & 1 & 0 \\ 0 & 0 & 0 & 1 \end{bmatrix}$$

The third parameter necessary to define the conic projection model is the focal length, f, between the x-ray source 115 and the image plane. The homogeneous transformation that represents the conic projection of points in space relative to coordinate frame I onto the image plane is represented as $$P = \begin{bmatrix} 1 & 0 & 0 & 0 \\ 0 & 1 & 0 & 0 \\ 0 & 0 & 1 & 0 \\ 0 & 0 & -\frac{1}{f} & 1 \end{bmatrix}$$

The parameters $t_x$, $t_y$, and f are determined preferably by a calibration process employing a grid 170 similar to the one previously described but with localizing emitters 171 mounted at known locations relative to the grid holes 172. Once the mapping parameters have been calculated, the grid 170 is held at an intermediate distance between the x-ray source 115 and the x-ray imager 114 while an x-ray image of the grid 170 is acquired and the poses of the grid 170 and x-ray imager 114 are measured by the optical localizer 120. Alternatively, the pose of the grid 170 may be known by mounting it relative to the x-ray imager 114 with a jig of known dimensions. In this case, the grid localizing emitters 171 may be omitted from the grid housing.

Next, the image processing techniques previously described are used to find the centers of the grid holes 172 in the x-ray images. The inverse mapping functions are then used to find the corresponding grid hole center locations on the image plane with respect to coordinate frame C.

The projection of the center of a physical hole, $^{C}p_i'$, onto the image plane can also be found with respect to coordinate frame C by the conic projection equation $$^{C}p_i' = {^{C}T_I} \cdot P \cdot {^{C}T_I}^{-1} \cdot {^{O}T_C}^{-1} \cdot {^{O}T_G} \cdot {^{G}p}$$

where $^{O}T_C^{-1}$ represents the inverse of the pose of the coordinate frame C on the image plane as measured by the optical localizer 120, $^{O}T_G$ represents the pose of the grid as measured by the optical localizer 120, and $^{G}p$ represents the location of the hole center with respect to the grid coordinate frame G as determined by design and manufacture.

The values of $^{C}p_i'$ as determined from the x-ray image are equated to the values of $^{C}p_i'$ as determined from the conic projection for each hole location (for i=1,2, . . . , n, where n is the number of hole centers viewable in the image). By applying a solution algorithm (such as singular value decomposition) the values of parameters $t_x$, $t_y$, and f are found.

The three conic projection parameters are valid for the C-arm 112 in its current pose. However, gravity induces various amounts of bending of the "C"-beam 113 as its orientation is changed. This results in a change in alignment of the x-ray source 115 and x-ray imager 114 and thus a change in $t_x$, $t_y$, and f. In the preferred embodiment, the conic projection calibration procedure is repeated for a number of C-arm orientations (e.g., C-arm inclination, $\phi_1$, of 0°, 30°, 60°, 90° and C-arm rotation, $\phi_2$, of 90°, −60°, −30°, 0°, 30°, 60°, 90°) with respect to the horizontal plane.

Figure 7:
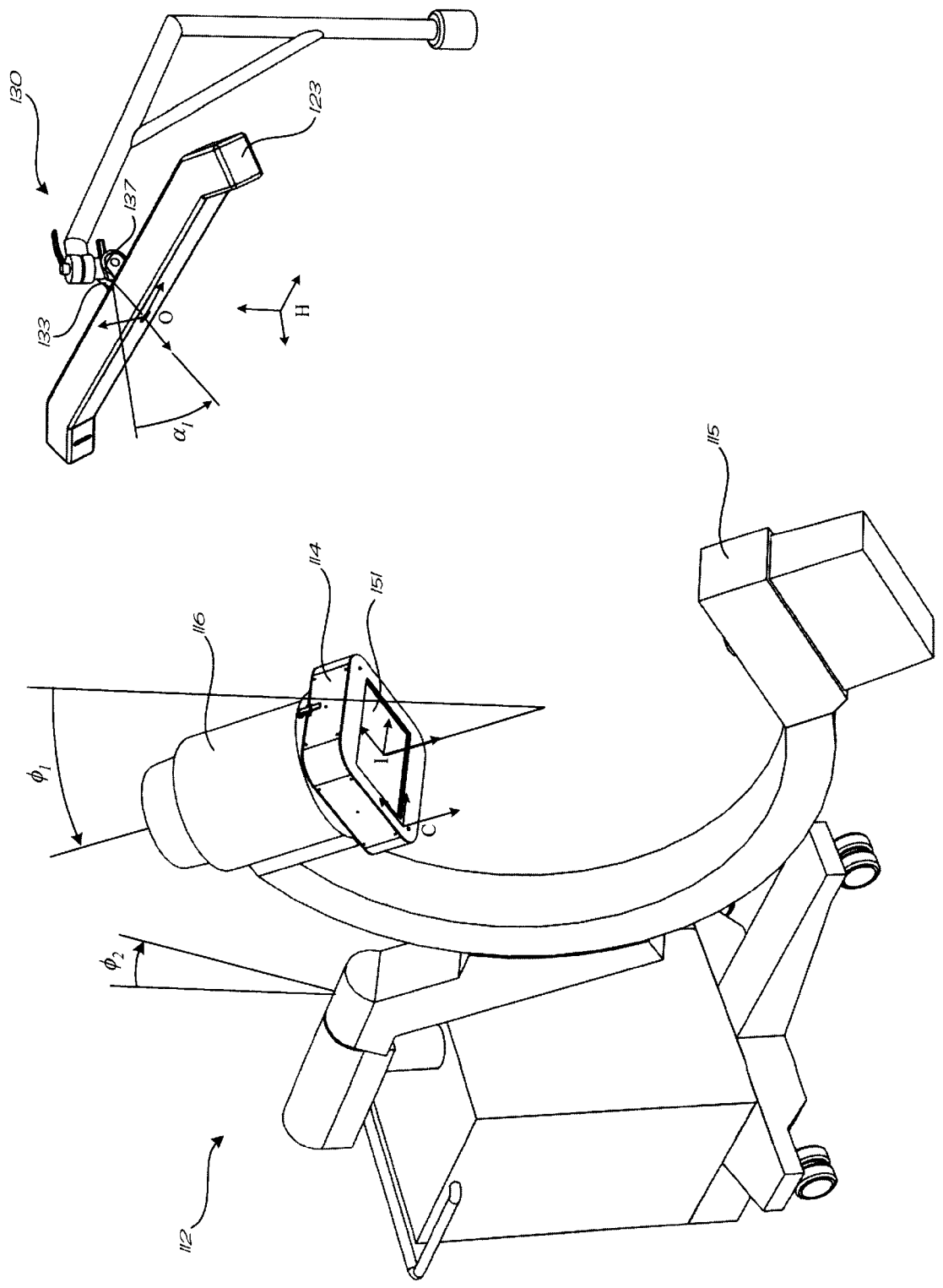
FIG. 7 is a perspective view of the C-arm with attached flat panel imager, and an optical localizer sensor unit and its support and mounting means.

Preferably, these C-arm orientation angles are determined from the C-arm pose data and from a transformation relating the optical localizer sensor unit to the horizontal plane. Turning to FIG. 7, a horizontal coordinate frame, H, is defined by a transformation, $^{H}T_O$, that represents the rotation of the coordinate frame, O, of the optical localizer sensor unit 123 by $\alpha_1$, the angle of inclination of the sensor unit 123 from the horizontal. The value of $\alpha_1$ is determined by reading the voltage, $v_1$, of the first potentiometer 137 on the mounting means 130 and interpolating a corresponding angular value from the potentiometer look up table. A homogenous transformation that represents the pose of the coordinate frame C of the C-arm's flat-panel imager 114 with respect to the horizontal coordinate frame H, is then given by the equation $$^{H}T_C = {^{H}T_O} \cdot {^{O}T_C}$$

The C-arm orientation angles, $\phi_1$ and $\phi_2$, can then be extracted from $^{H}T_C$. These steps are known in the art.

Alternatively the orientation of the C-arm relative to the horizontal plane may be represented by other notation methods including Euler angles or roll/pitch/yaw angles. Further, the C-arm orientation relative to horizontal may be obtained by other means including the mounting of the localizer sensor unit in a horizontal position, the measurement of the inclination of the sensor unit with an inclinometer (i.e., an electomechanical device that measures and reports an object's inclination from the horizontal), or the measurement of the orientation of the C-arm directly with a pair of inclinometers.

The three conic projection parameters, along with the corresponding C-arm orientation, are then stored in the long term memory of the system controller 121. These data are then available for later use to determine appropriate conic projection parameters for any arbitrary C-arm orientation. Alternatively, further sets of conic projection parameters, or other parameters necessary for the modeling the imaging chain, may be derived and stored corresponding to variables other than the pose of the C-arm. These also would be available later to permit the accurate calculation of the imaging model for any given pose or values of the other variables.

Figure 8A:
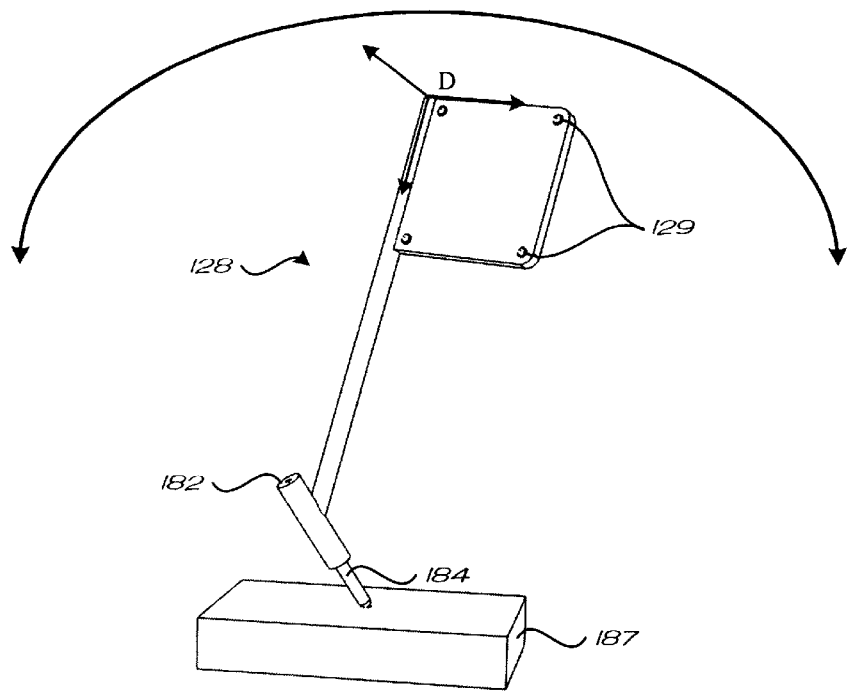
FIGS. 8a and 8b are perspective views of the drill guide with different length calibration shafts.
Figure 8B:
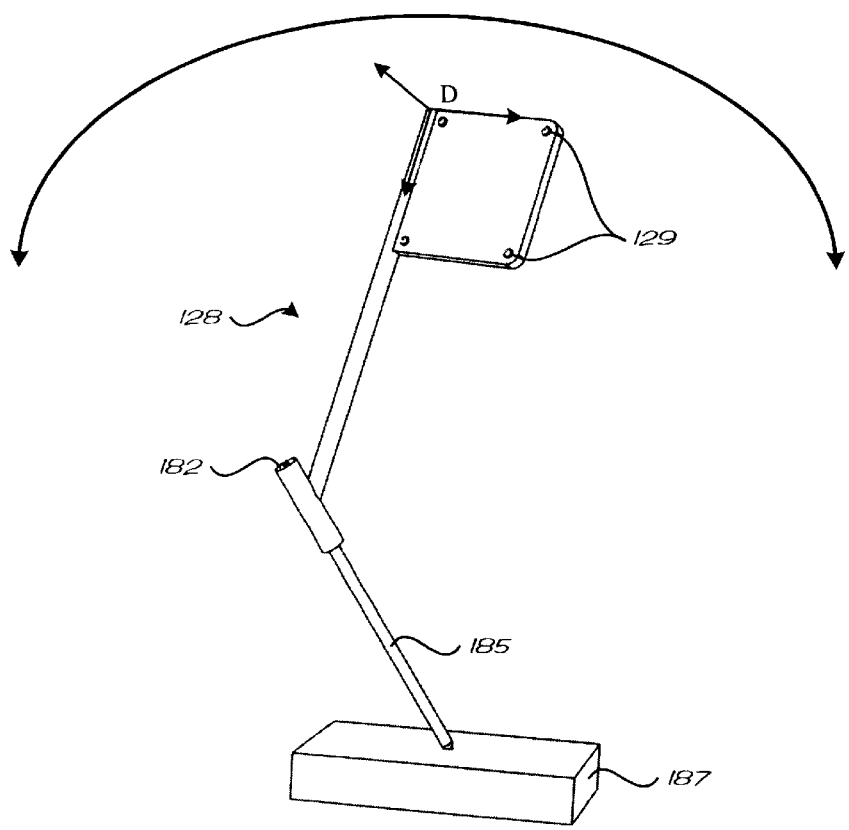

In accordance with the invention, the representation of the surgical tool must accurately relate to the tool itself. This requires that points used in the tool representation be accurately located with respect to the tool's localizing emitters. Turning to FIGS. 8a and 8b, a drill guide 128 is shown comprising a guide bore 182 mounted in a known pose relative to localizing emitters 129. A tool coordinate frame, D, is chosen and the locations of the localizing emitters 129 are determined relative to it, preferably from the precision of the tool design and manufacture. Alternatively, the optical localizer 120 can be used to determine the relative locations of the localizing emitters 129. Preferably, a description of this relationship, a tool emitter location data file, is encoded into a computer data file and stored in the long term memory of the optical localizer controller 124.

In the preferred embodiment, two points defining the trajectory of the bore 182 of a drill guide 128 are found by means of a calibration procedure that employs calibration shafts 184, 185 and the optical localizer 120. Two points, p and q (with respect to coordinate frame D), are identified that lie along the trajectory of the bore 182 of the drill guide 128. A calibration shaft 184 with a pointed tip at one end is inserted snugly into the bore 182 of the drill guide 128. The tip of the metal shaft 184 is inserted into a small dimple included in a rigid calibration fixture 187. This constrains the center of the tip of the calibration shaft 184 to a single point location regardless of the orientation of the drill guide 128. The body of the drill guide 128 is rotated and moved about this point with a spherical motion, while the locations of the drill guide's localizing emitters 129 are monitored by the optical localizer 120 and recorded.

The position of the tip of the calibration shaft 184 with respect to the optical localizer 120 can be represented by the equation $$^Op = {^OT_D} \cdot {^Dp}$$

where $^OT_D$ represents the pose of tool coordinate frame D as measured by the optical localizer 120, and $^Dp$ represents the unknown location of the tip of the calibration shaft 184 with respect to the tool coordinate frame D. Since the tip position is rigidly fixed and therefore constant, a least squares method such as single value decomposition may be used in conjunction with a plurality of tool poses to determine the tip position, p, with respect to the tool coordinate frame D. This process is repeated with a second, different length, calibration shaft 185 in order to find a second point, q, along the trajectory of the bore 182 of the drill guide 128.

In the preferred embodiment, a three dimensional vertex and line graphics model is generated that represents the trajectory of the tool's guide bore 182 with respect to coordinate frame D. Alternatively, the tool model may describe any physical features of the tool as well as any imaginary points or lines (such as center lines or measurement marks) that may be useful to the surgeon. The generation of such 3D models is known in the art. Further, the tool model may contain other data including surface data or two dimensional information such as text messages, measurement templates or other graphics. The tool model is encoded into a computer data file and stored in the long term memory of the system controller 121.

Figure 9:
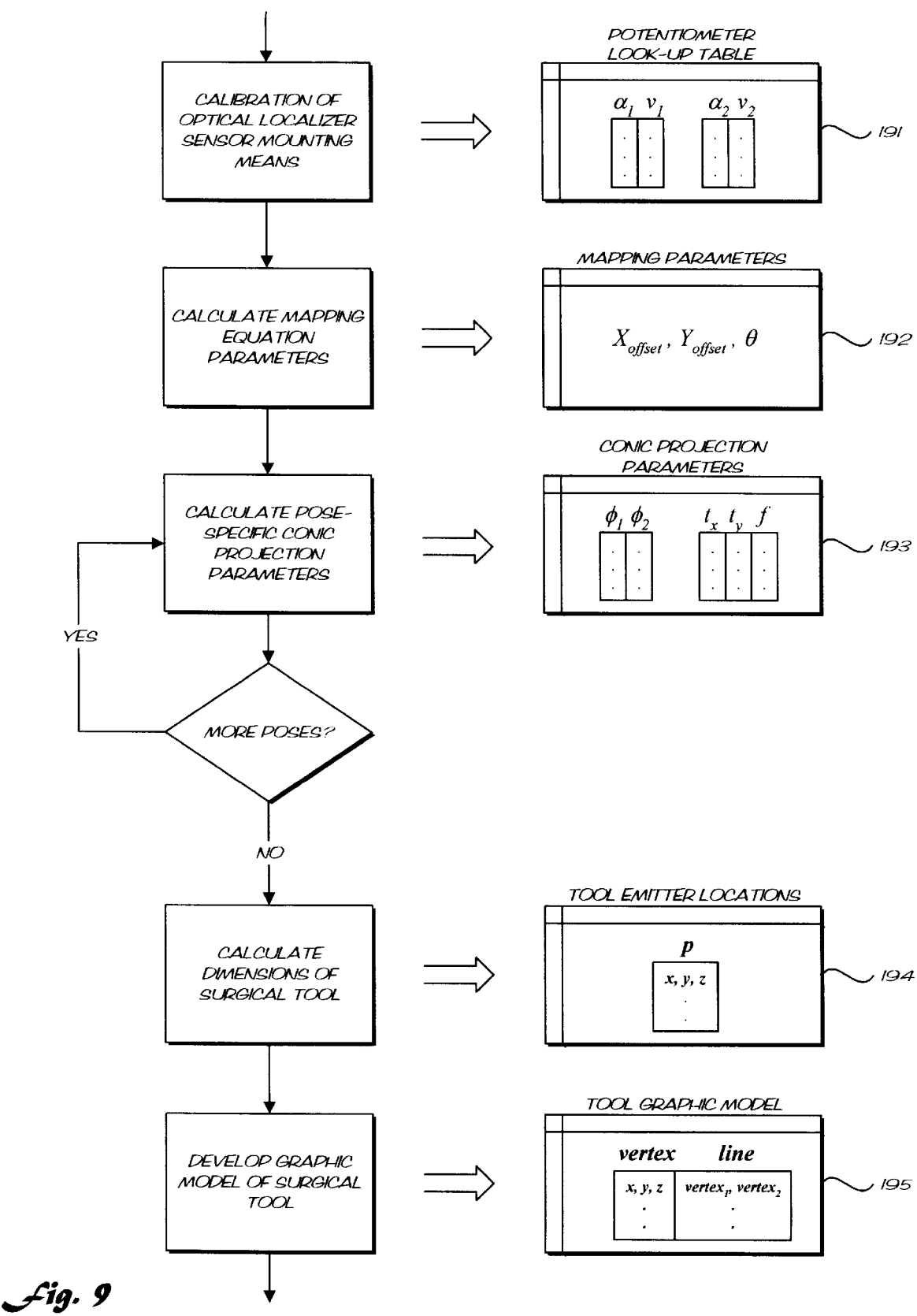
FIG. 9 is a diagrammatic illustration of the calibration procedure and the resulting data sets.

In summary, FIG. 9 shows how several calibration procedures are performed prior to system use in the operating room. A set of potentiometer voltages with corresponding angular position values is determined for both joints of the optical localizer sensor mounting means 130 and stored as look up tables 191 in the long term memory of the system controller 121. The mapping parameters $x_{offset}$, $y_{offset}$ and $\theta$, 192, are calculated and also stored in long term system memory. A set of conic projection model parameters $t_x$, $t_y$, and f, with associated pose data, $\phi_1$ and $\phi_2$, 193, are determined and stored in long term system memory. A tool emitter location data file 194, describing the locations of the localizing emitters 129 relative to a tool coordinate frame D, is generated and stored in the long term memory of the optical localizer controller 124. Following calculation of two points along the functional trajectory of the tool 128, a tool model data file 195 that defines a 3D representation of the surgical tool 128 is generated and stored in long term system memory.

System Function During Surgery

Figure 10:
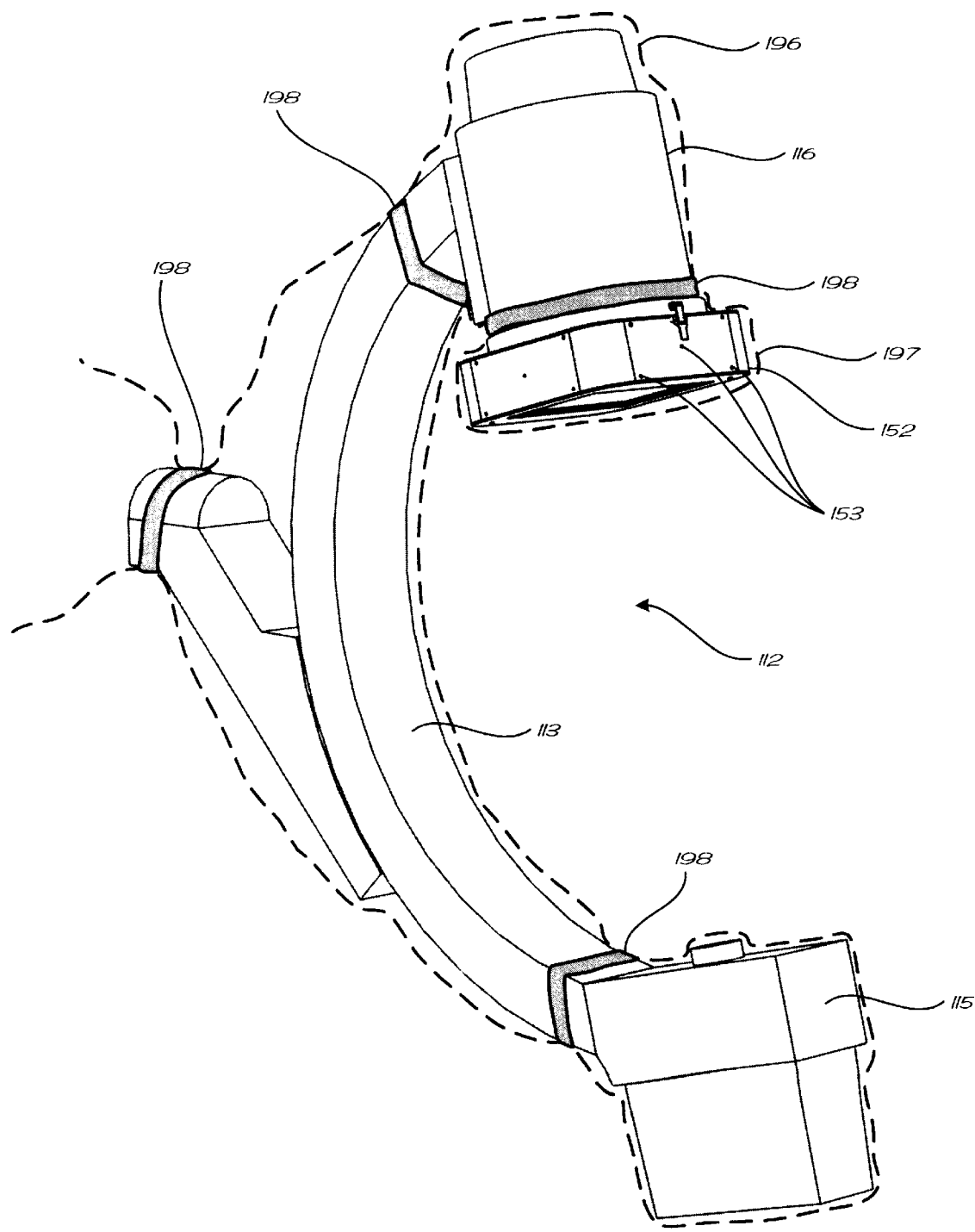
FIG. 10 is a perspective view of a partial C-arm with attached flat panel imager, and with transparent drape.

Once the calibration steps have been performed and necessary data sets have been stored in memory, the system is ready for use in surgery. Prior to the procedure, the C-arm 112 is covered by a transparent sterile drape 196, as shown in FIG. 10. The drape takes the form of a large "bag" with one corner modified to form a pouch 197 that duplicates the shape and size of the flat panel imager housing 152. The material used in the pouch portion 197 is slightly elastic and is transparent to infrared light. The pouch portion 197 is manufactured to be slightly smaller in circumference than the flat panel imager housing 152 such that the drape material stretches slightly to fit flush and flat against the localizing emitters 153. Optional elastic straps 198 hold the remainder of the drape away from the surgical site and the localizing emitters 153. Alternatively, the pouch portion 197 may be relatively inelastic and of nearly identical size to the flat panel imager housing 153. A retaining ring (not shown) may be used to secure the pouch portion 197 to the housing 152 and may further help maintain the transparent material flush and flat to the localizing emitters 153.

In the preferred embodiment, the system is used during a procedure to fix an intertrochanteric hip fracture. The surgical step with which this invention is described is that of the insertion of a guide pin into the proximal femur. Referring to FIG. 1, the patient is placed on a standard fracture table 102 with the femur 101 held in proper position. The C-arm 112, with attached flat panel x-ray imager 114, is positioned relative to the patient so as to image the fractured hip. After sterile preparation and draping, the patient's fractured femur 101 is imaged in a front view (anteroposterior or AP) and in a side view (lateral).

Figure 11:
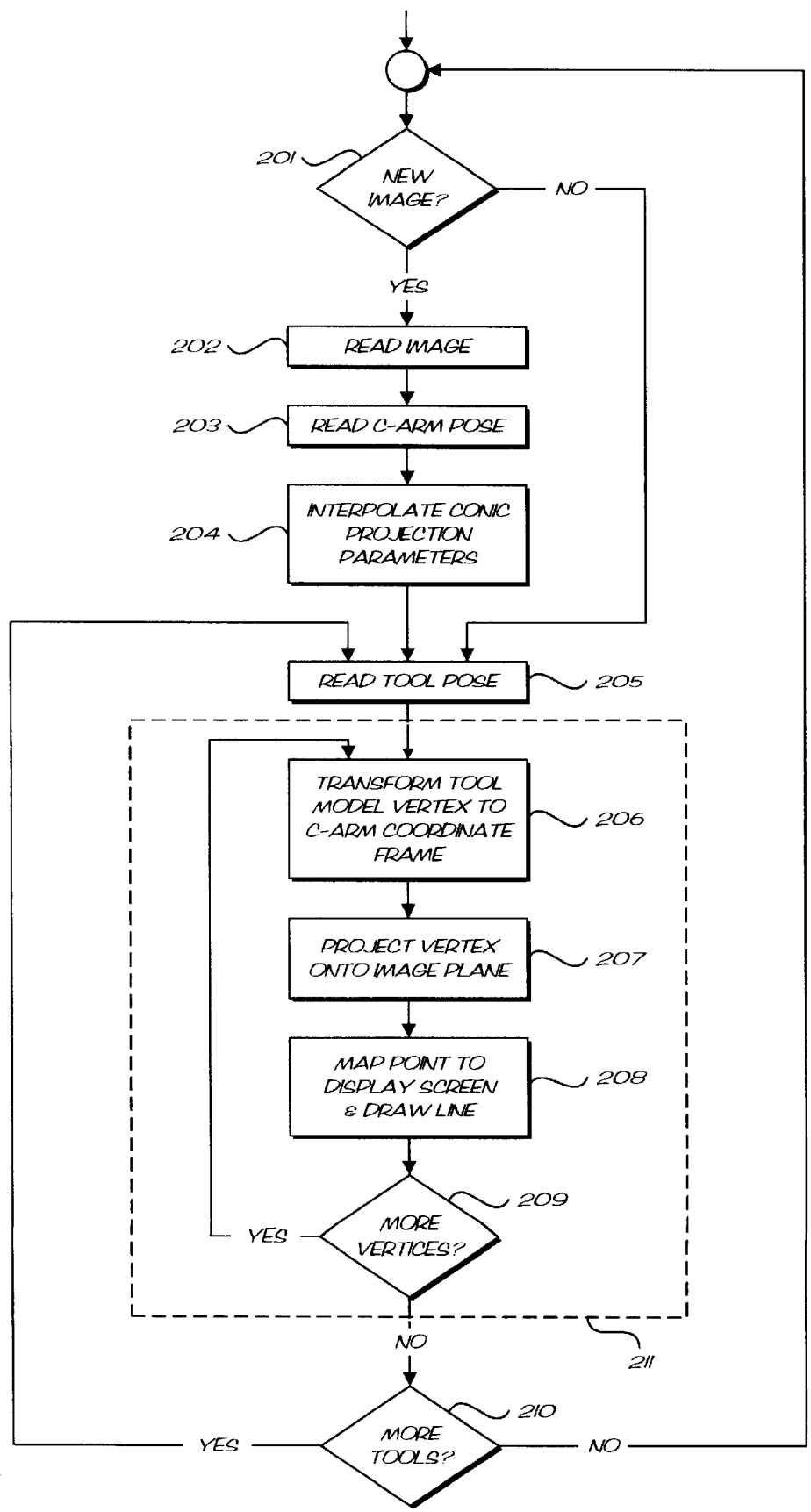
FIG. 11 is a diagrammatic illustration of the software operation during the surgical procedure.

Referring to FIGS. 1 and 11, there are several steps in the process of superimposing a tool representation on x-ray images. For each image generated, the x-ray source 115 of the C-arm 112 is activated. Preferably the system controller 121 knows when a new image is ready to be acquired 201 by sensing an increase in x-ray energy striking the imager 151. (Alternatively, this can be sensed by the activation of a signal line from the C-arm 112.) The system controller 121 then reads 202 the new image into its memory while the pose of the C-arm 112, (i.e., the pose of the flat panel imager 114, represented by $^{O}T_C$) is measured 203 by the optical localizer 120. Next, orientation angles relative to the horizontal plane, $\alpha_1$ and $\alpha_2$, are calculated from the pose of the C-arm and the inclination of the optical localizer sensor unit, as was described previously. Alternatively, these angles may be calculated using inclinometers.

Next an interpolation of the parameters calculated for the previously obtained C-arm poses is performed 204 to determine the pose-specific values of the conic projection parameters, $t_x$, $t_y$, and f, corresponding to the orientation angles, $\phi_1$ and $\phi_2$, of the current C-arm pose. These calculations are all known in the art. Preferably, conic projection parameters and the C-arm pose are likewise determined and stored for a second image that is displayed simultaneously with the first image.

Alternatively, localizing emitters are present on both the x-ray source and x-ray receiver end of the C-arm. Previously stored transformations allow the calculation of the origins of the x-ray source and image planes from which the conic projection parameters, $t_x$, $t_y$, and f, are readily derived.

After exposing the lateral aspect of the proximal femur, the surgeon positions the drill guide 128 against the bone 101. The pose of the drill guide 128 is measured 205 by the optical localizer 120, a representation of the tool at that pose is calculated 206, is passed through the conic projection model 207 and the mapping model 208 and then superimposed on the appropriate image. For each image acquired, a separate graphic representation of the trajectory is thus generated if the drill guide's trajectory passes through the volume in space where the x-ray passed when that image was acquired.

Figure 12:
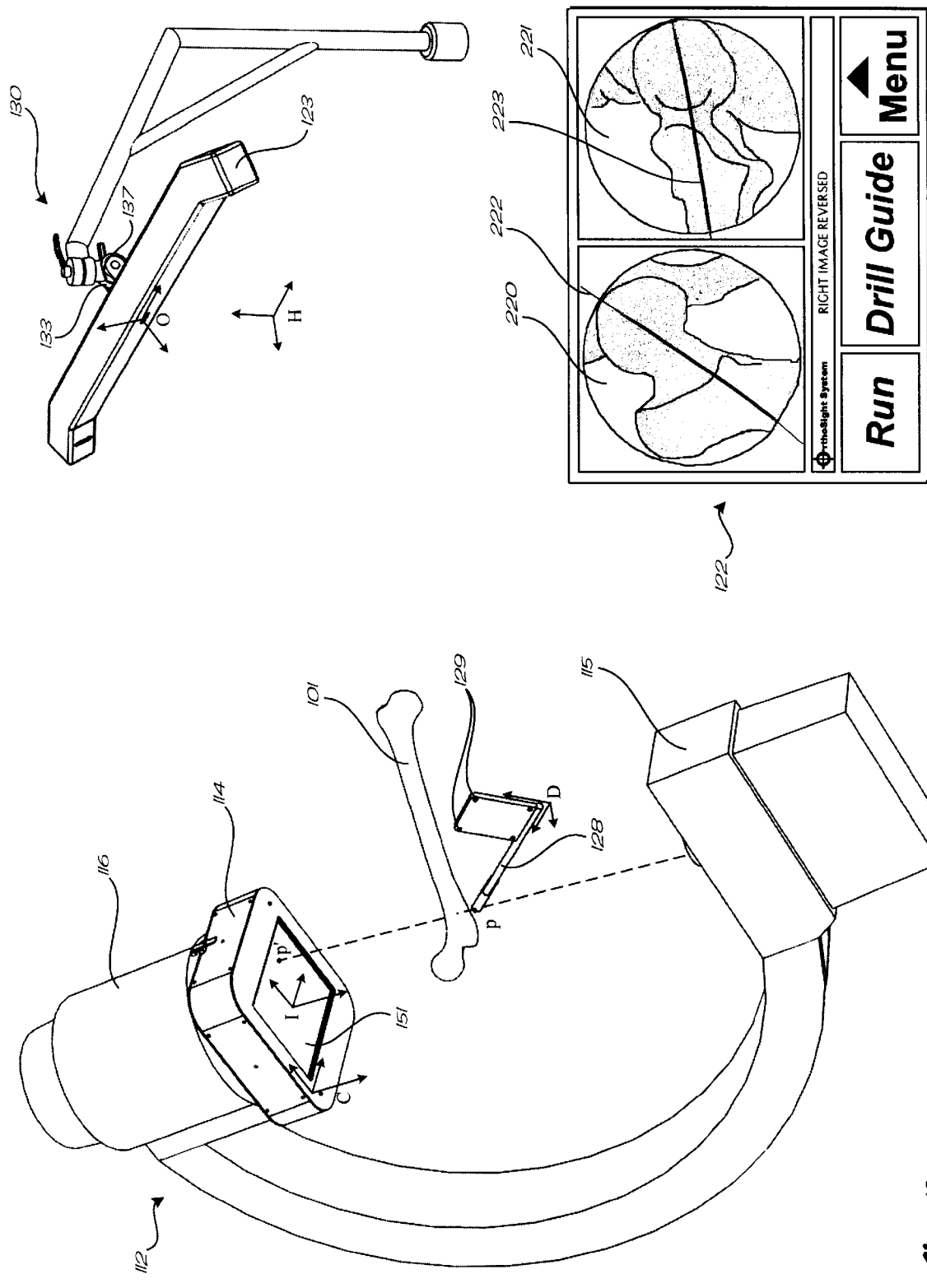
FIG. 12 is a perspective view of a partial C-arm with attached flat panel imager, optical localizer sensor unit and its support structure and mounting means, the surgical tool, a femur and the display screen containing images and graphics.

In the preferred embodiment, shown in FIG. 12, the localizing emitters 129 on the drill guide 128 are viewed by the optical localizer receiving unit 123 and the pose of the drill guide's coordinate frame D is determined. Based on the pose of the drill guide 128, the virtual locations in space of the previously stored vertices of the drill guide representation are calculated. The location in space of a point on the drill guide, p, relative to the digital x-ray imager coordinate frame C can be determined by the equation $$^{C}p = {^{O}T_C}^{-1} \cdot {^{O}T_D} \cdot {^{D}p}$$

where $^{O}T_C^{-1}$ represents the pose of the optical localizer sensor unit 123 relative to the x-ray imager 151, $^{O}T_D$ represents the pose of the drill guide 128 with respect to the optical localizer sensor unit 123, and $^{D}p$ represents a point in the drill guide 3D model relative to its coordinate frame D. The projection and mapping of the vertex from a virtual point in space to a location on the monitor screen 122 is then modeled by the conic projection and mapping equations. The projection of point p onto the image plane is accomplished by the equation $$^{C}p' = {^{C}T_I} \cdot p \cdot {^{C}T_I}^{-1} \cdot {^{C}p}$$

The mapping functions F(x,y) and G(x,y) are then applied to $^{C}p'$ to yield the screen position of that point (vertex) of the tool model. This is repeated for each vertex representing the trajectory, and lines are generated to connect appropriate vertices, until that part of the tool trajectory that falls within each image's corresponding x-ray volume is superimposed on that image.

In the preferred embodiment, the surgeon views the continuously updated 2D tool representations (tool cursors) 222, 223 representing the drill guide trajectory superimposed on the AP image 220 and lateral image 221, while aligning the drill guide 128 to the proper position. Once the drill guide 128 is aligned, a guide pin (not shown) is drilled into the bone 101. The surgery is then completed in the usual fashion including the reaming of the screw hole, the insertion of the hip screw, the application of a mated plate on the lateral femur 101, the optional insertion of a compression screw, and the closure of the incision.

Optical Localizer with Two Sensor Units

Figure 13:
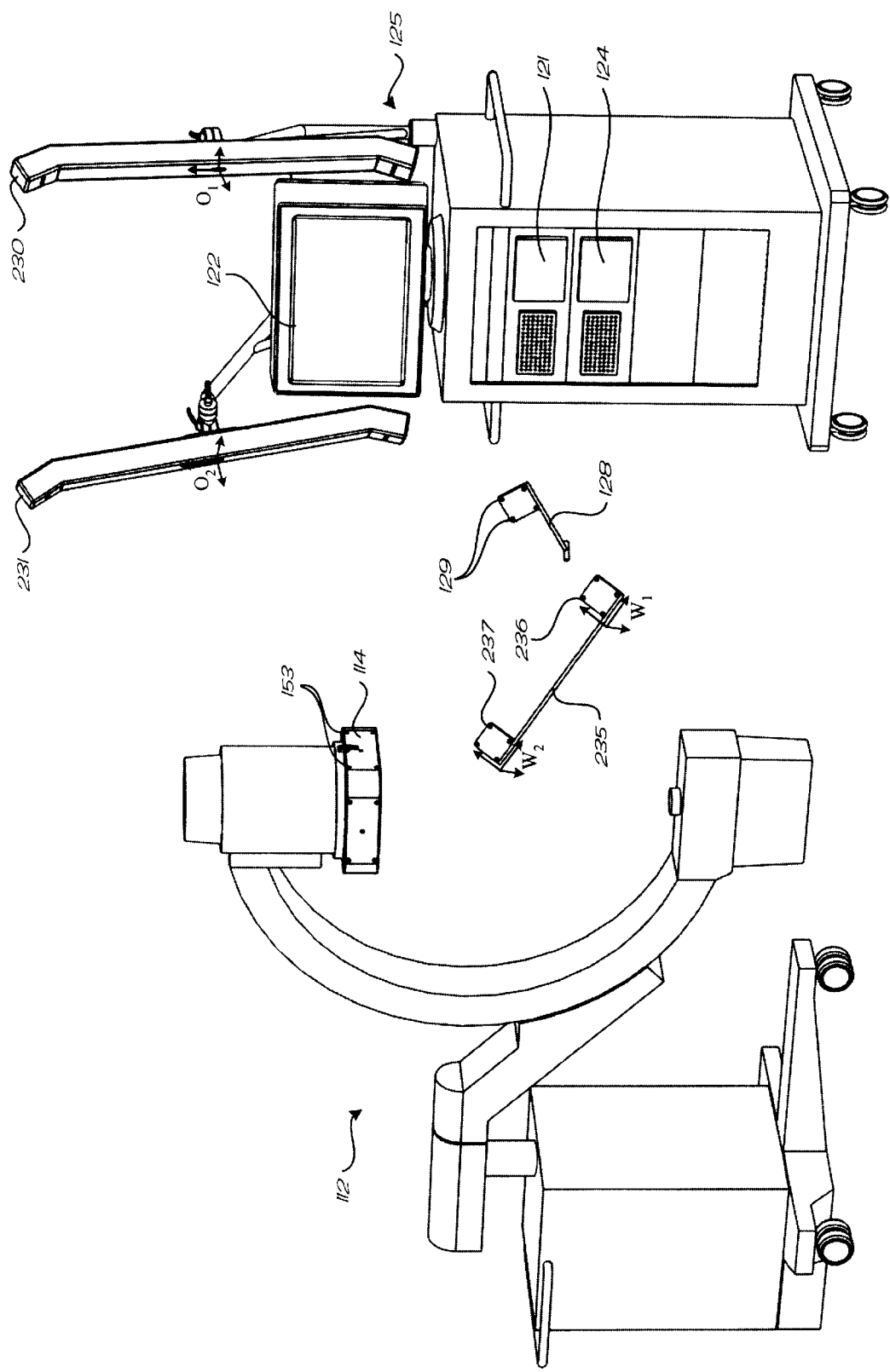
FIG. 13 is a perspective view of the system cart with two optical localizer sensors, a partial C-arm with attached flat panel imager, the surgical tool and a registration wand.

In an alternative embodiment, seen in FIG. 13, the localizing device 120 comprises a first sensor unit 230 and a second sensor unit 231. Preferably a single localizer controller 124 is used but, alternatively, two controllers, one for each sensor unit, may be used. Prior to use in surgery, the sensor units 230, 231 are aimed at the intended fields of view and locked into position. For the intertrochanteric fracture, one sensor is aimed at the localizing emitters 153 mounted on the C-arm 112 while the other sensor is aimed at the surgical field to track the surgical tools 128.

Alternatively, especially for other procedures, the sensor units 230,231 may be aimed in a different manner, either with or without overlapping fields of view. The redundancy inherent in overlapping fields of view can provide increased accuracy and improved immunity to obstructions.

In order to use the pose data from both sensors, the physical relationship between the two sensors 230, 231 must be determined. This is accomplished with a registration object 235 containing a plurality of localizing emitters 236, 237. Preferably, the registration object takes the form of a wand 235 and is held such that at least three non-collinear localizing emitters 236, 237 are seen simultaneously by both sensors 230, 231 and their poses recorded. The intersensor transformation giving the pose of the second sensor 231 relative to the first sensor 230 is calculated by the equation $$^{O1}T_{O2} = {^{O1}T_{W1}} \cdot {^{W1}T_{W2}} \cdot {^{O2}T_{W2}}^{-1}$$

where $^{O1}T_{W1}$ represents the pose of the first set of wand localizing emitters 236 as seen by the first localizer 230, $^{W1}T_{W2}$ represents the relationship of the second set of localizing emitters 237 relative to the first set 236 as known by design of the wand 235, and $^{O2}T_{W2}^{-1}$ represents the inverse of the pose of the second set of wand localizing emitters 237 as seen by the second localizer 231.

Alternatively, only a single emitter need be seen by each sensor if the distance between the localizing emitters is fixed and known, and three or more samples are obtained. Further if the localizer sensor units 230, 231 are aimed with overlapping fields of view, a single emitter or set of localizing emitters may be used. In this case the registration object need not take the elongated form of a wand, but may be any shape. The flat panel imager 114 or a surgical tool 128 containing a plurality of localizing emitters may also be used for this registration process.

During the surgical procedure, a sterile drape (not shown) is hung horizontally between the C-arm 112 and the surgical field such that only the first sensor 230 can accurately view the surgical instruments 128 on one side of the drape, while only the second sensor 231 can accurately view the C-arm 112 on the other side of the drape. Preferably, when an image is acquired, the optical localizer controller 124 strobes the localizing emitters 153 associated with the C-arm 112, and strobes the localizing emitters 129 associated with the surgical tool 128 the remainder of the time. Thus, the pose of the tool 128 is derived from data from the first sensor unit 230 and the pose of the C-arm 112 is derived from data from the second sensor unit.

Alternatively, other algorithms for deriving emitter positions from the data from the sensor units may be employed. For example, when the fields of view of the sensor units overlap, this algorithm may involve averaging redundant position data, preference for position data closest to the center of one sensor's field of view, or the use of redundant sensor data to determine emitter position.

So that all pose data have the same reference frame, the C-arm pose data, as measured by the second sensor 231, are converted to the frame of the first sensor 230 with the equation $$^{O1}T_C = {^{O1}T_{O2}} \cdot {^{O2}T_C}$$

where $^{O1}T_{O2}$ represents the previously determined intersensor transformation and $^{O2}T_C$ represents the C-arm pose with respect to the second sensor 231. The C-arm pose and tool poses with respect to the first optical localizer sensor 230 then are used in the same manner as described for the one sensor unit system.

Body Part Motion Detection and Correction

In accordance with a feature of the invention, a means is provided for the detection of motion of the body part being operated upon and for the partial correction of tool cursor superposition. This is desirable in cases where the immobility of the body part cannot be insured. The position of the imaged body part is tracked by means of a device attached to the body part during the procedure. Any detected motion of the body part is evaluated relative to the plane of each stored image. For small motions, tool representations superimposed on the images are translated and rotated by an identical amount. For motions larger than a predetermined value, an error condition is raised and the surgeon alerted.

Figure 14:
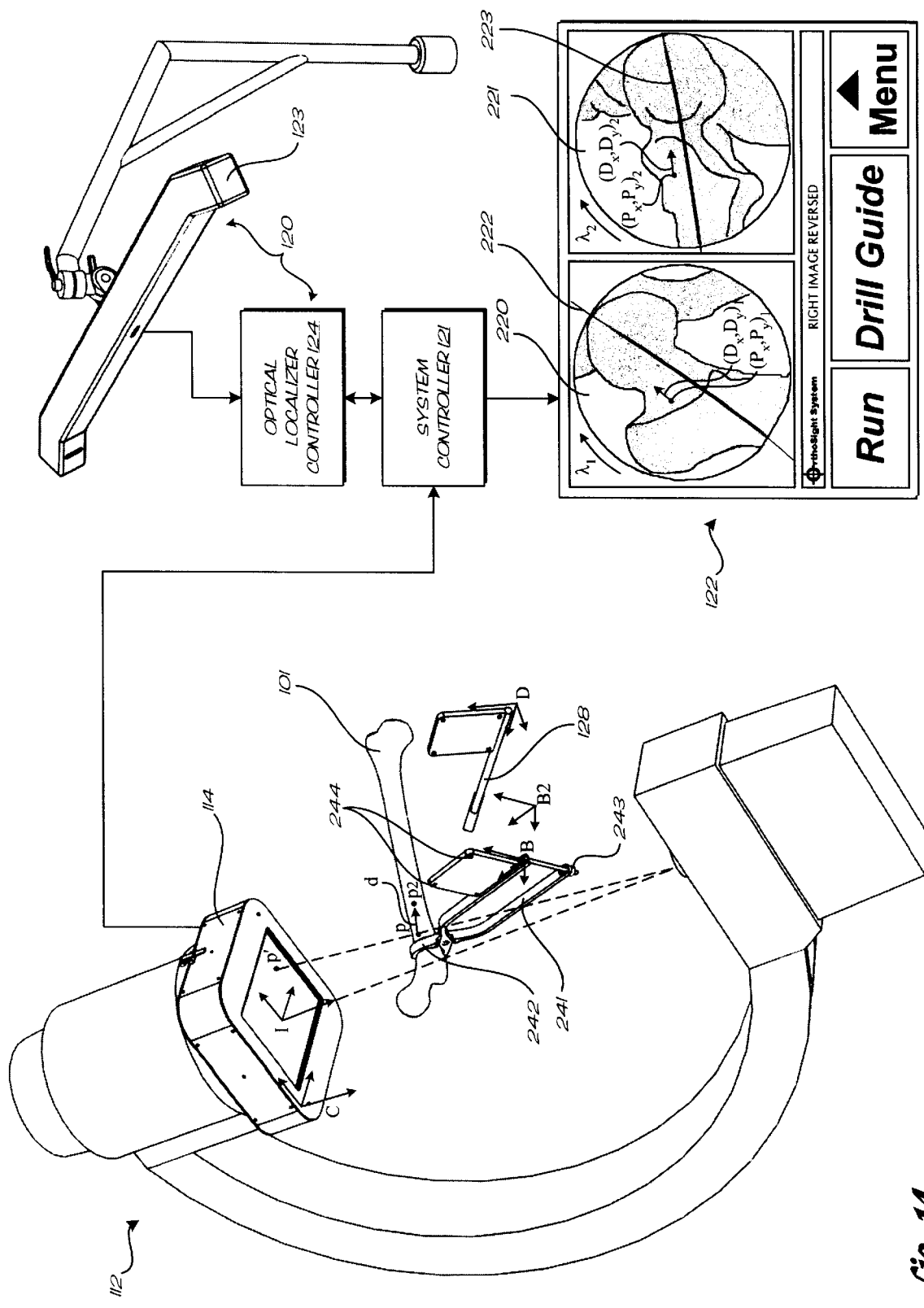
FIG. 14 is a perspective view of the bone tracking clamp attached to a femur, partial C-arm with attached flat panel imager, the surgical tool, the optical localizer sensor unit, and display screen containing images and graphics.

In the preferred embodiment, shown in FIG. 14, the tracking device is a clamp 241 that attaches to the femur 101. The tracking device 241 comprises toothed jaws 242 that grip the femur 101 and can be locked in a tightened position by a tightening device such as a screw 243, thus holding the tracking device 241 rigidly fixed relative to the femur 101. The tracking device 241 further comprises a plurality of localizing emitters 244. Alternatively, the tracking device may comprise a bone screw or screws, an intramedullary device, or any other suitable means for rigidly affixing to the body part during the surgical procedure. Dimension data, previously determined during device design and manufacture, relating the locations of the localizing emitters 244 relative to a tracking clamp coordinate frame, B, are stored in the long term memory of the system controller 121.

In surgery, the tracking clamp 241 is attached to the shaft of the femur 101 in a location proximal to the intended site of guide pin insertion. As each image is obtained, the pose of the tracking clamp 241 is measured by the optical localizer 120 and is stored as the initial reference pose of the tracking device 241 for that image.

Next, a location in space is identified as the intended point of surgery, p. This point may be inside the body part, outside the body part, or on its surface. Preferably this is calculated by finding the point of intersection (or the midpoint between skew lines) of the z-axes of the image plane coordinate frames, I, for two acquired images. A separate value, $^Cp$, of this one point is calculated relative to the x-ray imager 114 for each C-arm pose corresponding to an acquired image.

Alternatively, the intended point of surgery may be specified by other means including the position of the tip of the tracking device 241, the position of the tip of the surgical tool 128, the position indicated by the surgeon with a tracked probe, or points indicated by the surgeon on the system monitor screen.

The position of the intended point of surgery is calculated relative to the bone tracking clamp's coordinate frame, B, by the equation $$^Bp = {^OT_B}^{-1} \cdot {^OT_C} \cdot {^Cp}$$

where $^OT_B^{-1}$ represents the inverse of the pose of the bone tracking clamp 241 as measured by the optical localizer 120, $^OT_C$ represents the pose of the C-arm 112 as measured by the optical localizer 120, and $^Cp$ is the vector representing the intended point of surgery with respect to the imaging device coordinate frame. This calculation is performed once using either C-arm pose. Next, the location of the intended point of surgery in image space, $(P_x, P_y)$, is found for each acquired image by transforming $^Cp$ using the conic projection model and the mapping equations.

As the optical localizer 120 continuously reads the pose of the surgical tool 128, it also continuously reads the pose of the bone tracking clamp 241. Translation of the intended point of surgery p with respect to the x-ray imager coordinate frame C is determined by changes in the pose of the tracking clamp 241 and the equation $$d = {^OT_C}^{-1} \cdot {^OT_{B2}} \cdot {^Bp} - {^Cp}$$

where $^OT_{B2}$ represents the new pose of the bone tracking clamp 241 as measured by the optical localizer 120, and $^Cp$ represents the original pose (i.e., at the time of image acquisition) of the intended point of surgery. The translational motion of the intended point of surgery parallel to the image plane is given by the elements ($d_x$, $d_y$) of vector d. This calculation is performed for each image that has been acquired.

Rotational motion of the body part 101 around the intended point of surgery is the same as the rotational motion of the rigidly attached bone tracking clamp 241. The rotation of the tracking clamp 241 with respect to the coordinate frame of the image plane, I, is the same as rotation with respect to the coordinate frame of the imaging device, C, and is given by the equation $$^CR_{B2B} = {^OR_C}^{-1} \cdot {^OR_{B2}} \cdot {^OR_B}^{-1} \cdot {^OR_C}$$

where $^OR_C$ and $^OR_C^{-1}$ are rotation matrices representing the orientation of the C-arm 112 as measured by the optical localizer 120, and $^OR_{B2}$ and $^OR_B$ are rotation matrices representing the current and initial orientations of the bone tracking clamp 241 as measured by the optical localizer 120. The angular rotation of the bone tracking clamp 241 on the image plane is given by the equation $$\lambda = \tan^{-1}\left(\frac{n_y}{n_x}\right)$$

where $n_x$ and $n_y$ are elements of the rotation equation $^CR_{B2B}$. This calculation is performed for each image that has been acquired.

In the preferred embodiment, if the translation of the intended point of surgery parallel to any image plane is greater than a prespecified distance (e.g., 5 mm.) or the rotation about the intended point of surgery parallel to any image plane is greater than a prespecified angular value (e.g., 2 degrees), then that image is considered invalid. The surgeon is informed of this condition by an image invalidation graphic (e.g., the border of the image turns red) and the tool cursor disappears for that image. Alternatively, exceeding the invalidation threshold for any image may result in the invalidation of all images. The invalidation thresholds may be adjusted for different surgeries and for surgeon preference.

If the translation and rotation of the intended point of surgery are both below their respective image invalidation thresholds, the tool cursors are then adjusted to compensate. Tool cursor points to be superimposed on the image are translated in image space by an amount given by the equation $$\begin{pmatrix} D_x \\ D_y \end{pmatrix} = -\mu \frac{f}{f - {}^c p_z} \begin{pmatrix} d_x \\ d_y \end{pmatrix}$$

where $(d_x, d_y)$ represents the distance the bone tracking clamp 241 has shifted parallel to the image plane, f is the imaging device focal length determined during calibration, ${}^c p_z$ represents the distance between the image plane and the intended point of surgery and $\mu$ represents the imager linear pixel density. Finally, the tool cursor points are rotated in image space by an amount $\lambda$ about the intended point of surgery $(P_x, P_y)$.

Alternatively, the bone tracking device 241 may include only one or two localizing emitters 244. In these cases only the translation of the bone 101, or the translation and rotation about a single axis, respectively, is calculable. This may be acceptable for cases where the bone 101 is unlikely to rotate significantly. Alternatively, the bone tracking device 241 may function as a dynamic reference frame wherein the poses of other tracked devices are measured relative to it. However, while the poses of the tools can be accurately tracked for large movements, any objects that do not have attached localizing emitters (e.g., fracture fragments, soft tissue, other implants, tools or bones) may not be accurately located in the images.

Surgical Tool as System Input Device

In accordance with a feature of the invention, a means is provided for the surgeon to modify the functioning of the system during surgery by pointing the surgical tool 128 at previously defined selection fields on the monitor screen 122. By using the surgical tool 128 as a pointing device, the surgeon can command the system and respond to its inquiries directly without an intermediate operator, a sterilizable input device, or other equipment such as a footswitch. Further, calculating the actual intersection of the trajectory of a pointing tool with the plane of the screen 122, and defining physical areas of the screen 122 as selection fields, the surgeon is provided with a clearly defined and intuitive means for providing input to the system and which may be used simultaneously as an image guided surgical tool and input device without the need for a switching device or for the removal of the tool from the surgical field.

Figure 15:
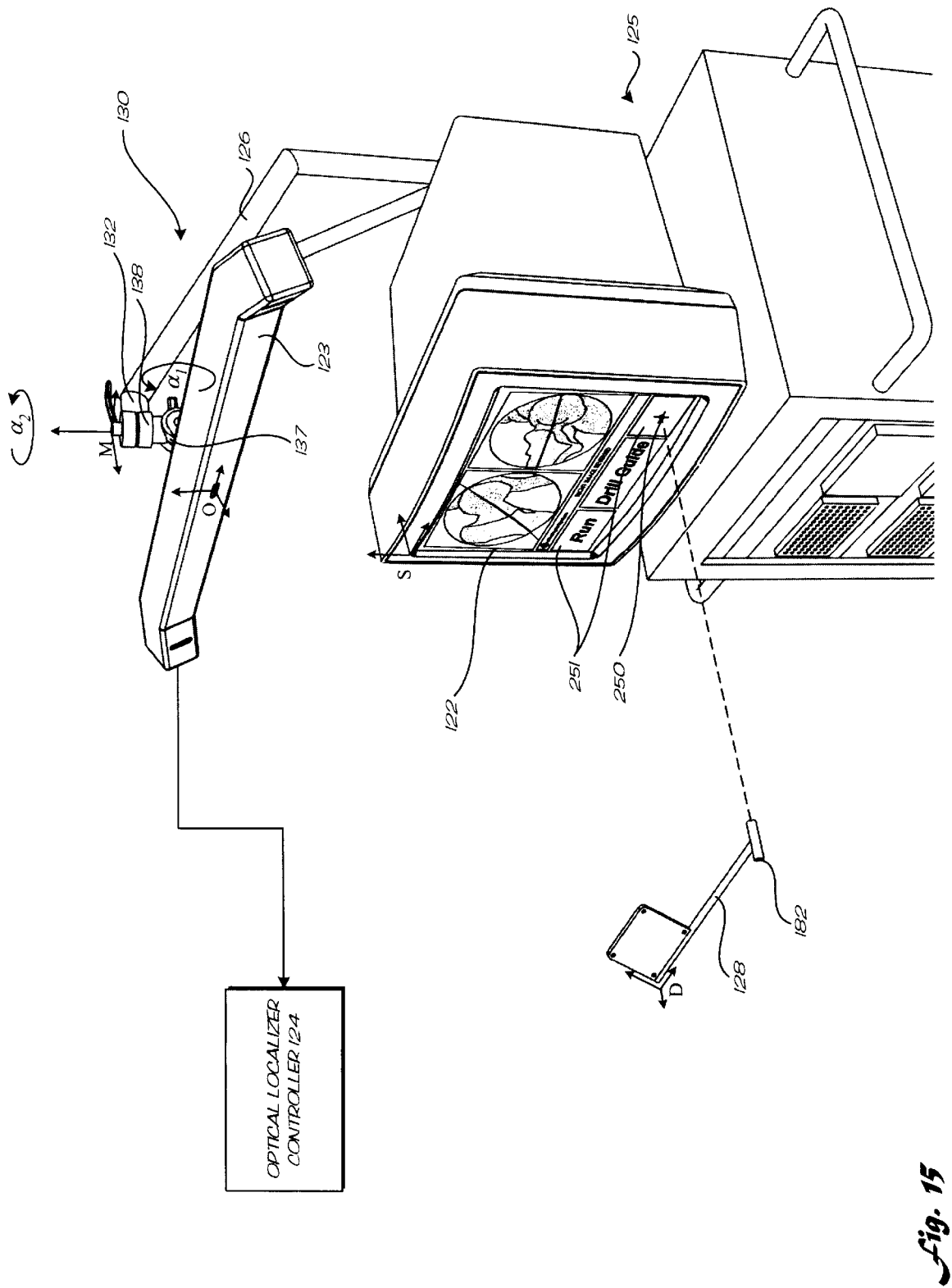
FIG. 15 is a perspective view of the surgical tool and partial system cart with system monitor and optical localizer sensor unit support structure and mounting means.

Referring to FIG. 15, whenever the surgical tool 128 is in the field of view of the optical localizer receiving unit 123, the pose of its coordinate frame is continuously calculated. The pose of the surgical tool 128 with respect to the coordinate frame of the system monitor screen 122 is then calculated. Preferably, this calculation includes dimension data from the design and manufacture of the system cart 125 and support arm 126, as well as the dimensions of the mounting means 130 for the optical localizer sensor 123 and the voltages of the potentiometers 137, 138. The potentiometer voltages (which are read at system initialization and periodically thereafter) are used to determine an interpolated angular value from the previously stored look up tables. Once the sensor unit inclination angle, $\alpha_1$, and the horizontal rotation, $\alpha_2$, are determined, it is possible to determine the pose of the tool's coordinate frame with respect to the system monitor screen coordinate frame, S, with the equation $${}^S T_D = {}^S T_M \cdot {}^M T_O \cdot {}^O T_D$$

where ${}^S T_M$ represents the homogeneous transformation from the system monitor screen coordinate system to the base of the mounting means, ${}^M T_O$ represents the homogeneous transformation of the optical localizer sensor unit 123 with respect to the support arm attachment point 132 of the mounting means 130 and is a function of $\alpha_1$ and $\alpha_2$, and ${}^O T_D$ represents the pose of the tool 128 as measured by the optical localizer 120. The derivation of these homogeneous transformations is known in the art.

Alternatively, the pose of the display screen 122 may be determined by means other than those involving only the pose of the localizer support structure 126 and mounting means 130. For example, a calibration process that involves pointing the tool 128 at the corners of the screen 122 may also be used. Further, any means that determines the pose of the tool 128 with respect to the system monitor 122 may be employed without departing from the instant invention.

The intersection of a line with a plane can be found by setting to zero the dot product of a matrix representation of the plane and a parametric vector equation of the line. This calculation is significantly simplified by careful assignment of the coordinate frames. In the preferred embodiment, the tool coordinate frame D is chosen such that the z-axis coincides with the pointing axis of the tool (i.e., the bore 182 of a drill guide 128). The screen coordinate frame S is selected such that its origin is in the upper left hand corner of the screen 122, the x-axis is directed toward the upper right corner of the screen 122, the y-axis is directed down toward the lower left corner of the screen 122, and the z-axis is directed inward to the screen 122. This results in equations for the x,y position of the intersection of the trajectory of the tool 128 with the plane of the screen 122

$$x = -\frac{a_x p_z}{a_z} + p_x \quad y = -\frac{a_y p_z}{a_z} + p_y$$

where x and y represent locations on the plane of the monitor screen 122 with respect to the screen coordinate system, S, and $a_x, a_y, a_z, p_x, p_y, p_z$ are elements of the homogeneous transformation matrix ${}^S T_D$.

Alternatively, the pointing axis may be assigned along any part of the tool 128 including its longest dimension, its handle or any prominent feature. Any coordinate frame may be assigned to the pointing axis of the tool 128, and the coordinate frame of the screen 122 may be assigned differently, albeit with an increase in computational complexity.

In the preferred embodiment a selection cursor (e.g., a crosshairs) 250 is displayed on the screen 122 at the point of intersection between the tool trajectory and the plane of the screen 122 and moves in response to changes in pose of the surgical tool 128. Specific rectangular areas of the system monitor screen are defined as selection fields 251 and rectangles are drawn on the screen 122 at these locations. When the selection cursor 250 is moved by the surgeon into one of the rectangles, the field 251 is considered to be selected. Before the action corresponding to the selected field 251 can be taken, an activation criteria must be met. Preferably this criterion is the continuous selection of the field 251 for a given period of time (e.g., two seconds). Alternatively, the activation criterion may be the pressing of a footswitch, trigger or other button, or it may involve voice commands or a characteristic motion of the tool 128 (e.g., motion toward the screen 122). Additionally, the selection field 251 may change color when selected and change color again when the activation criteria are met.

Alternatively, the selection cursor 250 may be replaced by any icon or may not be displayed at all. Also the selection fields may be assigned any size or shape, as may the corresponding on screen rectangles. Further, the selection fields and plane of the screen may be scaled smaller or larger (even extending beyond the screen boundary) to improve the surgeon's ability to accurately and easily visualize the selection cursor and select the appropriate fields. It should be recognized that some inaccuracies are introduced by the use of potentiometers 137, 138 in determining the pose of the optical localizer sensor unit 123, by modeling the system monitor screen 122 as a flat plane, and by the use of an external protractor to determine the sensor unit's orientation during calibration. These inaccuracies, however, are minor and easily overcome by the closed loop nature of the interface. That is, the surgeon will easily make minor corrections to the orientation of the surgical tool 128 until feedback is received indicating that a specific field 251 is selected.

Verification of System Accuracy

In accordance with another feature of the invention, a means is provided for verifying the accurate functioning of the system. At the time of image acquisition the pose of the surgical tools in the field of view of the optical localizer 120 is recorded. If the verification feature is enabled, a surgical tool 128 held in the x-ray field will cause a cursor of that tool 128 to be superimposed on the acquired image. This tool cursor is generated using the previously described tool model, conic projection equations and mapping functions and remains stationary on the screen until a termination criteria is met. During this time, the surgeon visually verifies that the computer generated tool cursor overlays, to a sufficient degree of accuracy, the silhouette of the radiopaque tool in the x-ray images. By assessing alignment of the tool in the x-ray image and its cursor in two nearly orthogonal images, the three dimensional accuracy of the system to both location and orientation can be verified.

Figure 16:
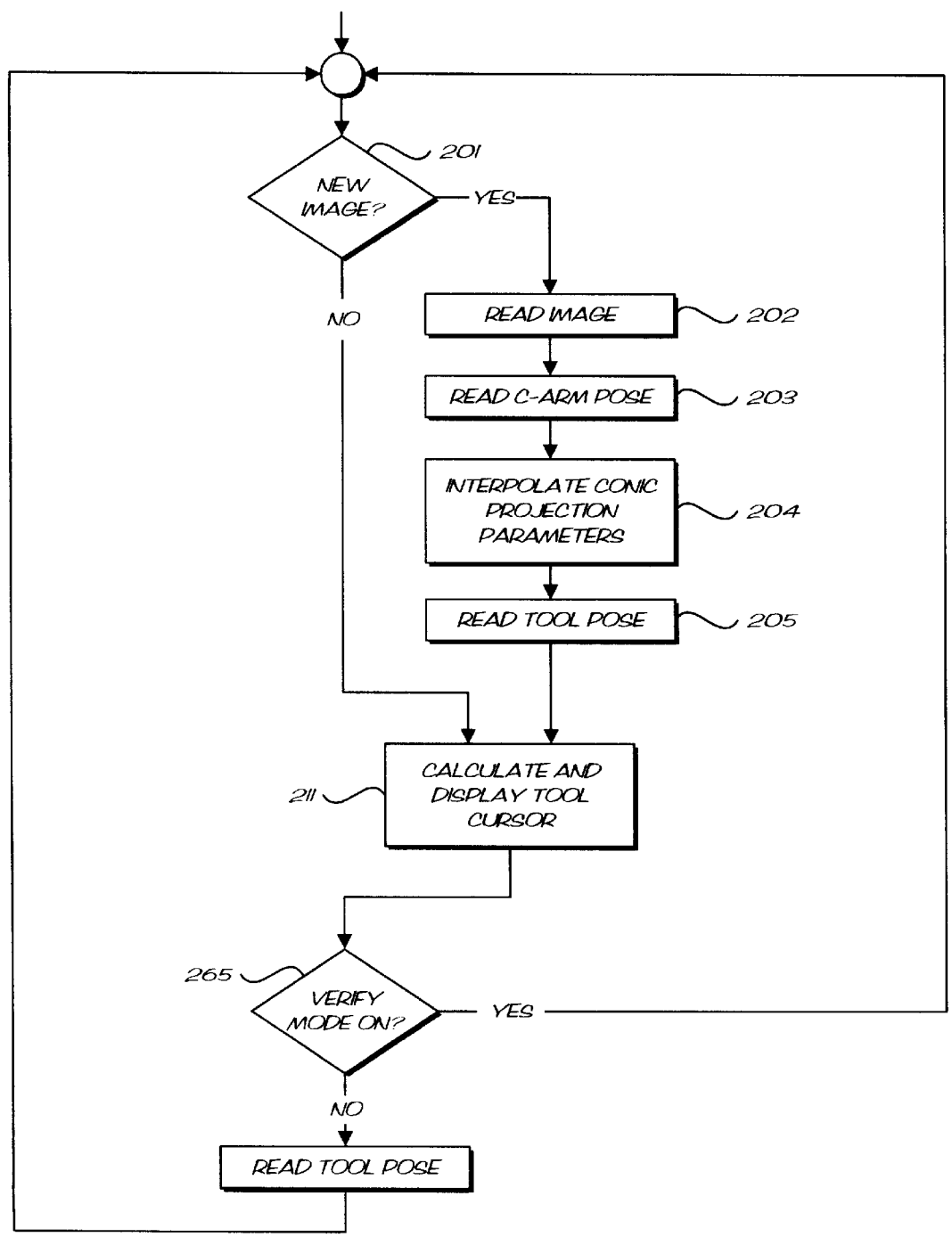
FIG. 16 is diagrammatic illustration of the software operation during verification mode.

In the preferred embodiment, the verification feature is automatically enabled when the surgical system is initialized. Alternatively, the feature could be initially disabled and then activated at the request of the operator. With the feature enabled, as shown schematically in FIG. 16, the pose of any surgical tool visible to the optical localizer is measured 205 at the time an image is acquired 202, 203, 204 and its associated data stored in memory. The tool pose data is used as previously described to generate a tool cursor on the image 211. Specifically, the tool pose and tool model are used to calculate the position in space of vertices that represent the tool, the conic projection model and previously determined parameters are used to project the vertices onto the image plane of the x-ray imager, and the mapping model and previously determined parameters convert them to pixels on the system monitor display screen.

Since both the pose of this tool cursor and the image were acquired at the same time, the precision with which the graphic representation aligns with the actual x-ray image of the tool indicates the correct functioning of the system and the accuracy of the imaging model and parameters. This verification tool cursor is superimposed on the image and is not updated as new pose data for the tool is acquired. Instead, it remains stationary on the screen until a termination criteria is met and the verification feature is disabled 265, giving the operator time to verify the accuracy of its positioning on both images. In the preferred embodiment, the termination criteria is an input signal from the surgeon. This preferably takes the form of the activation of a screen selection field with the surgical tool. Alternatively, the verification representation may be displayed for a specified period of time before it is discontinued or some other termination criterion applied. During the time the verification feature is enabled, the interactive, real-time tool cursor optionally may be displayed.

In the preferred embodiment, the tool cursor that is displayed during verification is the same one that is displayed during the surgical procedure. Alternatively, any tool representation may be used. For example, the verification tool representation may include extra markings that more precisely demonstrate the features of a tool, it may contain markings to facilitate measurement of errors, or it may present a simplified version for ease of viewing.

Computer Assisted Surgery System without Fluoroscopic Input

In accordance with an alternative embodiment of the invention, a system is described for use in orthopaedic surgery procedures that do not typically require images intraoperatively. The system assists the surgeon in aligning a first surgical tool relative to a second tool by displaying continuously updated representations of the tools relative to each other in one or more projections. In this embodiment, the x-ray imager and C-arm are removed. The system comprises a controller, a system monitor or, an optical localizer, and two surgical tools with localizing emitters.

Figure 17:
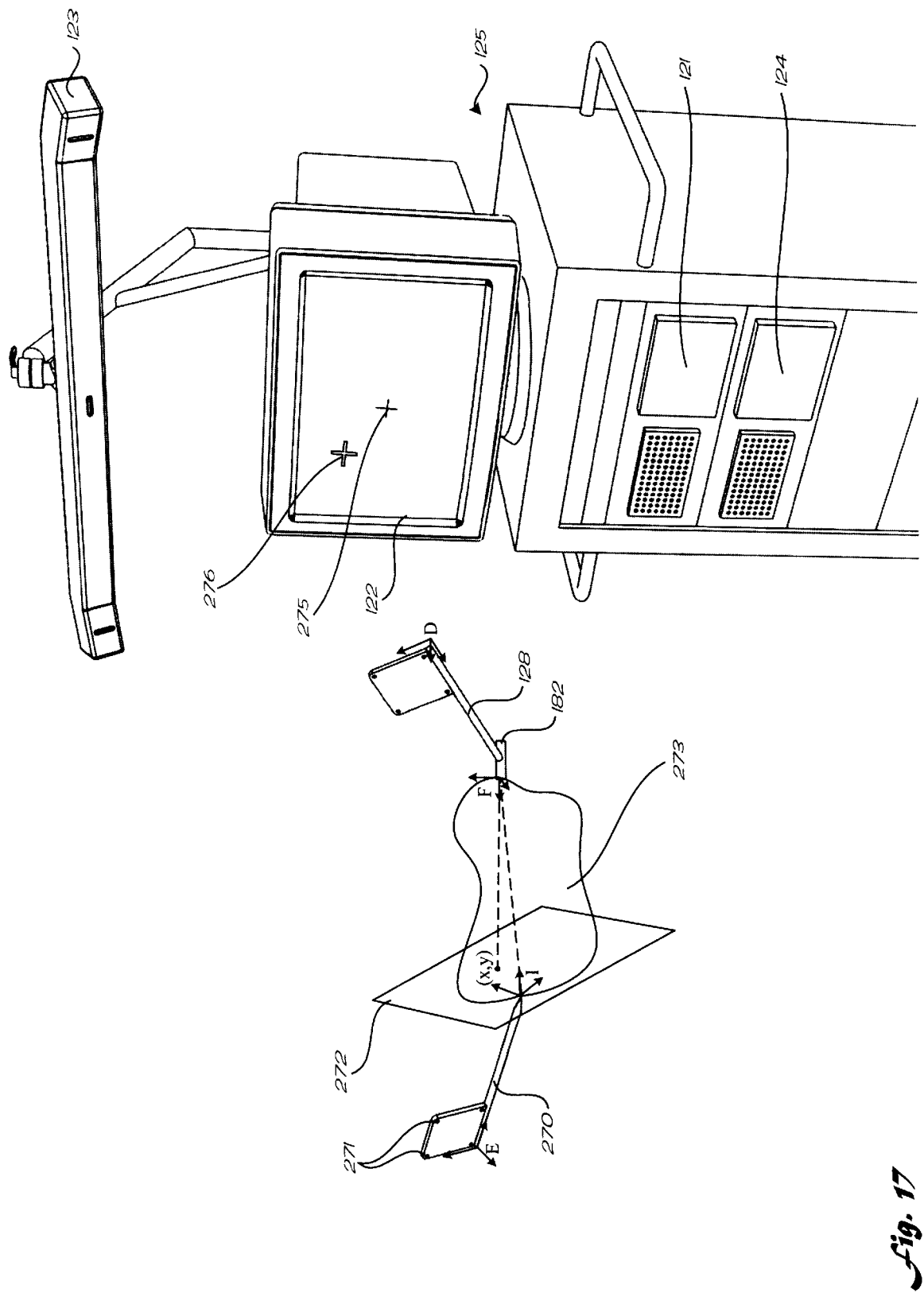
FIG. 17 is a perspective view of a targeting probe, drill guide and partial system cart showing the optical localizer sensor unit, system monitor screen, and controllers.

A preferred application for this system is that of drilling a hole through a bone (e.g., placement of longitudinal holes in the patella for purposes of patellar tendon repair). As shown in FIG. 17, the tip of a targeting probe 270 with localizing emitters 271 is placed against the bony anatomy 273 at the intended exit point of the hole while the tip of a drill guide 128 is held at the intended entry point. A picture is displayed on the system monitor 122 in which the target probe is represented as a fixed crosshairs 275 and the trajectory of the drill guide is represented as a second crosshairs 276 which move on the screen in response to reorientation of the drill guide 128. When the picture representing the two crosshairs 275, 276 are aligned on the screen 122, the trajectory of the drill guide 128 is passing through the tip of the probe 270. By advancing a drill bit (not shown) through the bore of the drill guide 128, the surgeon creates a hole in the bony anatomy 273 from the intended entry point to intended exit point.

In order to generate the target and trajectory cursors on the display 122, the first step is the measurement of the tools' poses by the optical localizer 123,124. The tip of the probe 270 relative to the optical localizer receiving unit 123 is determined from the pose of the probe coordinate frame E and the known dimensions of the probe 270. The pose of coordinate frame F of the tip of the drill guide 128 relative to the optical localizer receiving unit, $^OT_F$, is determined from the pose of the drill guide coordinate frame D and the known dimensions of the drill guide 128.

The next step is the determination of the pose of the plane upon which the picture is formed. For the drilling of a hole in bone, this picture plane 272 is selected preferably such that it passes through the tip of the probe 270 and is perpendicular to a line between the tip of the probe 270 and the tip of the drill guide 128. A coordinate frame representing the picture plane 272 with respect to the optical localizer receiving unit 123 is defined that has its origin at the target probe tip, its z-axis along the line between the probe and drill guide tips, and a horizontal x-axis and vertical y-axis with its xy plane representing the picture plane 272. Using techniques known in the art, a homogeneous transformation representing the picture plane coordinate frame $^OT_I$ is developed from the probe and drill guide tip locations. Once the picture plane 272 is defined, the pose of the coordinate frame of the drill guide 128 can be found relative to the coordinate frame of the picture plane 272 by the equation $$^IT_F = {^OT_I}^{-1} \cdot {^OT_F}$$

The next step is the calculation of where the trajectory of the drill guide 128 intersects the picture plane 272. The intersection of a line with a plane can be found by setting to zero the dot product of a matrix representation of the plane and a parametric vector equation of the line. Assuming the trajectory of the drill guide 128 corresponds to the z-axis of coordinate frame F, the equations for the x,y position of the intersection of the tool trajectory with the picture plane are $$x = -\frac{a_x p_z}{a_z} + p_x \quad y = -\frac{a_y p_z}{a_z} + p_y$$

where x and y represent positions with respect to the picture is plane coordinate system and $a_x$, $a_y$, $a_z$, $p_x$, $p_y$, $p_z$ are elements of the homogeneous transformation matrix $^IT_F$. Alternatively, the trajectory axis of the drill 128 may be assigned to any unit vector with respect to the tool's coordinate frame, and the coordinate frame of the picture plane 272 may be assigned differently, albeit with an increase in computational complexity.

The picture representing the tool alignment is then generated on the system monitor 122. Preferably, a stationary crosshairs 275 is placed in the center of the screen 122 representing the position of the tip of the target probe 270. The intersection of the drill trajectory with the picture plane 272 is represented on the screen 122 by a second crosshairs 276 which move as the drill guide 128 is reoriented. The mapping of the intersection of the trajectory with the picture plane onto the system monitor 122 is accomplished with linear equations. When the two crosshairs 275, 276 are aligned, it indicates that the trajectory of the drill guide 128 is passing through the tip of the target probe 270 and the surgeon may advance the drill.

Additionally, the distance between the tool tip and the target probe tip can be displayed as a bar graph or other graphic that represents the value of $p_z$ from the homogeneous transformation matrix $^IT_F$.

Alternatively, the two dimensional picture may be formed by another method such as conic projection or linear projection. Further, the picture plane 272 may be placed in any location relative to the first tool, the second tool, or some other reference frame. The xy axes of the coordinate frame of the picture plane 272 may be placed in any orientation.

The tools that are tracked and used in the generation of the picture may comprise surgical instruments, instruments to which are attached surgical implants, instruments attached to the bone, power tools or any other object containing localizing emitters. The tool representations generated for these objects may include stylized representations of important features, wireframe models of the object, or any other graphic representation that is appropriate for the application.

System Displaying Fluoroscopic Images and Non-fluoroscopic Pictures

In accordance with an alternative embodiment of the invention, a system is described that includes aspects of fluoroscopic and non-fluoroscopic computer assisted surgical systems. The system assists the surgeon by superimposing a graphic representation of a first surgical tool over x-ray images as well as with respect to a second surgical tool. Referring to FIG. 18, the system comprises a controller 121, a system monitor 122, an optical localizer 120, and two surgical tools 128, 280 with localizing emitters 129, 281 respectively. The system is used in conjunction with an x-ray source 115 and receiver 116, preferably a C-arm 112 with a digital flat panel imager 114.

A preferred application for this system is the drilling of a screw hole through the bone 101 and transverse holes 286 in the distal end of an intramedullary (IM) rod 285 inserted into a long bone 101. Once the IM rod 285 has been inserted into the bone 101, a tracking tool 280 containing localizing emitters 281 is attached to its proximal end to track the IM rod's pose. X-ray images 292, 293 of the distal portion of the IM rod 285 are then acquired. A graphic representation 290 of the drill guide 128 is superimposed over the x-ray images 292, 293 to assist the surgeon in selecting the appropriate entry point and in aligning the drill guide 128 in the coronal plane.

The system also assists the surgeon in achieving the proper drill guide orientation in the axial plane. A representation of a cross section 291 of the IM rod 285 at the level of a distal screw hole 286 is displayed separately and superimposed with the drill guide representation 290. When the drill guide trajectory is centered on the IM rod screw hole in the lateral x-ray image 292 and the orientation is centered on and parallel to the hole on the AP image 293 and on the cross section representation 291, the surgeon advances the drill.

For the portion of this embodiment that takes input from a fluoroscope 112, the image acquisition and superposition of the drill guide trajectory is accomplished in the same manner as previously described for the preferred embodiment. The same calibration procedures, conic projection model, mapping functions and transformations are used as with the preferred embodiment. (See FIGS. 1 to 12.)

Returning to FIG. 18, the display of the drill guide trajectory 290 in relation to a graphic representation 291 of the IM rod 285 and tracking tool 280 requires three steps. The first step is the generation of a computer model that relates the position of the distal screw holes 286 in the IM rod 285 to the localizing emitters 281 on the implant (IM rod) tracking tool 280. Since the tracking tool 280 must be reversibly attached to the IM rod 285, a repeatable and accurate attachment method is required. Preferably the IM rod tracking tool 280 screws into a threaded hole already provided at the proximal end of the IM rod 285 for use with the standard instrumentation (not shown) used to insert the rod into the bone. Notches on the proximal end of the IM rod 285, also provided for the standard insertion instruments, provide rotational stability and a known rotational relationship with the attached tracking tool 280. Alternatively, the tracking tool 280 may attach to other features of the IM rod 285 such as the proximal locking screw holes (not shown) or it may attach to an insertion tool already connected to the IM rod 285. The relationship of the attachment point on the IM rod tracking tool 280 to its localizing emitters 281 is accurately known by design of the tool and is stored in the controller's long term memory. The relationship of the transverse holes 286 in the IM rod 285 to the attachment point is accurately known from the design of the implant and is expressed as a three dimensional vertex and line graphics description relative to the tool coordinate frame and is stored in the controller's long term memory.

The second step is the determination of the pose of the plane 287 upon which the picture of the IM rod cross section 291 is formed. The pose of the IM rod tracking tool 280, and thus the pose of the IM rod 285, is measured by the optical localizer 120. The picture plane 287 is preferably defined as a plane perpendicular to the long axis of the IM rod 285. Its coordinate frame has its z-axis collinear with IM rod's long axis, its x-axis is horizontal, and its y-axis is vertical. The homogeneous transformation $^{E}T_{I}$ describes the coordinate frame of the picture plane 287 with respect to the tracking tool 280 and the IM rod 285. Its method of derivation is known in the art.

The final step is the projection of points representing the cross section of the IM rod 285 and the drill trajectory onto the picture plane 287 and their mapping to screen coordinates. The position in space of each vertex of the IM rod cross section representation is determined relative to the coordinate frame of the picture plane 287 by the equation $$^{I}p = {^{E}T_{I}}^{-1} \cdot {^{E}p}$$

where $^{E}p$ represents the vertices with respect to the tracking tool coordinate frame as listed in the data file defining the cross section representation. The position in space of each vertex of the drill guide trajectory is determined relative to the coordinate frame of the picture plane 287 by the equation $$^{I}p = {^{E}T_{I}}^{-1} \cdot {^{O}T_{E}}^{-1} \cdot {^{O}T_{D}} \cdot {^{D}p}$$

where $^{O}T_{E}^{-1}$ represents the inverse of the pose of the IM rod tracking tool 280 as measured by the optical localizer 120, $^{O}T_{D}$ represents the pose of the drill guide 128 as measured by the optical localizer 123, 124 and $^{D}p$ represents the vertices with respect to the drill guide coordinate frame as listed in the data file defining the drill guide representation.

With the axis of the picture plane 287 preferably defined as the z-axis, the projection of vertices onto the picture plane 287 is accomplished by using the x and y coordinates. The mapping into screen coordinates is accomplished with linear equations. Lines are also drawn to connect the vertices indicated in the graphic representation data file.

Alternatively, the picture plane 287 may be placed in any location relative to the first tool, the second tool or some other reference frame. The non-fluoroscopic two dimensional picture may be formed by a conic projection model or any other method that displays the relative poses of two or more objects. The tools that are tracked and used in the generation of the picture may comprise surgical instruments, instruments to which are mounted surgical implants, power tools or any other object containing localizing emitters. The tool representations generated for these objects may include stylized representations of important features, wireframe models of the object, or any other graphic representation that is appropriate for the application.

Additionally, a graphic representation of the IM rod 285 can be overlaid on the x-ray images to provide, for example, enhanced information as to the location of the transverse holes in a proximal-distal direction. This is accomplished by determining the pose of the IM rod tracking tool 280 and using the C-arm imaging model previously described to generate a representation of the IM rod 285 which is superimposed over the x-ray images 292, 293.

The implant tracking tool 280 may also serve the purpose of the bone tracking clamp previously described by monitoring the change in pose of the IM rod 285 and the femur 101 and causing a compensatory correction in the tool cursor 290 on the x-ray images 292,293 or, for larger motions of the tracking tool 280, the indication of an error. Alternatively, the implant tracking tool 280 may serve as a dynamic reference frame to which all tool poses are referenced allowing for full compensation for any motion of the bone 101 and IM rod 285.

The use of this system is not restricted to the insertion of interlocking screws in an IM rod, but may be applied to any surgery which may benefit from real-time feedback regarding poses of surgical tools relative to an imaged body part as well as to a second surgical tool or object.

The herein described system and features of the invention may be applied to surgeries and situations beyond those outlined in this description. Other surgeries to which this invention may be applied include, but are not limited to, other orthopaedic procedures such as percutaneous pinning of fractures and insertion of spinal pedicle screws, as well as non-orthopaedic procedures such as breast and other soft tissue biopsy. Further, applications to fields outside of medicine are contemplated. Other modifications and alternative embodiments of the invention are contemplated which do not depart from the spirit and scope of the invention as defined by the foregoing teachings and appended claims. It is intended that the claims cover all such modifications that fall within their scope.

We claim as our invention:

1. An image surgery system to enable a surgeon to move one or more surgical tools into a desired pose relative to a body part, comprising:
    an imaging device for generating a plurality of two-dimensional images of the body part, said imaging device including an x-ray generator and a flat panel x-ray imager;
    at least one surgical tool;
    a localizing device for measuring the pose of the surgical tool relative to the imaging device; and
    means for displaying representations of the surgical tool relative to the two-dimensional images of the body part.

2. The image guided surgery system of claim 1 wherein the imaging device is a C-arm fluoroscope.

3. The image guided surgery system of claim 1 wherein the flat panel x-ray imager is integral to the imaging device.

4. The image guided surgery system of claim 3 wherein the localizing device is an optical localizer and the imaging device is further outfitted with three or more localizing emitters, and the positions of said localizing emitters are measured by the optical localizer.

5. The image guided surgery system of claim 4 further comprising a sterile plastic drape, a section of the drape being adapted to cover a part of the imaging device containing localizing emitters, a portion of that section of the drape further adapted to fit flush and flat against the localizing emitters.

6. The image guided surgery system of claim 3 wherein the localizing device is an optical localizer and three or more localizing emitters are mounted in a housing that is attached to the imaging device, and the positions of said localizing emitters are measured by the optical localizer.

7. The image guided surgery system of claim 1 wherein the flat panel x-ray imager includes a housing attached to the imaging device.

8. The image guided surgery system of claim 7 wherein the localizing device is an optical localizer and the housing is further outfitted with three or more localizing emitters whose positions are measured by the optical localizer.

9. The image guided surgery system of claim 8 further comprising a sterile plastic drape, a section of the drape being adapted to cover a part of the flat panel x-ray imager housing having the localizing emitters affixed thereto, a portion of that section of the drape further adapted to fit flush and flat against the localizing emitters.

10. The image guided surgery system of claim 9 wherein the portion of the sterile drape fitting flush and flat against the localizing emitters is similar in dimension to the housing containing the emitters.

11. The image guided surgery system of claim 10 further wherein the housing is part of the imaging device.

12. The sterile drape of claim 9 further comprising a retaining ring that holds the drape against the housing and causes the drape to fit flush and flat against the localizing emitters.

13. The image guided surgery system of claim 1 wherein the localizing device is an electromagnetic localizer.

14. The image guided surgery system of claim 1 further comprising:
 a second surgical tool, and the pose of said second surgical tool is measured by the localizing device; and
 means for displaying a representation of the surgical tool relative to a representation of the second surgical tool independent of the images.

15. The image guided surgery system of claim 14 wherein either the surgical tool or the second surgical tool may be attached in a fixed and known relationship to an implant or other object.

16. The image guided surgery system of claim 14 wherein an axis of the surgical tool is to be aligned along a line between a point on the surgical tool and a reference point on the second surgical tool, and wherein a picture plane is defined that is perpendicular to said line and contains the reference point of the second surgical tool, and wherein alignment representations corresponding to the reference point on the second surgical tool and the intersection of said axis of the first surgical tool with the picture plane are displayed, such that the alignment representations are aligned when said axis of the surgical tool passes through the reference point of the second surgical tool.

17. The image guided surgery system of claim 1 further comprising:
 a tracking device comprising a tracked portion and a means for attaching to the body part to be operated upon;
 means for determining the motion of the tracking device in the plane of each two-dimensional image; and
 means for translating and rotating superimposed representations of surgical tools relative to each two-dimensional image to match the motion of the tracking device.

18. The image guided surgery system of claim 17 wherein the attaching means is a clamp.

19. The image guided surgery system of claim 17 wherein the attaching means is a plurality of screws.

20. The image guided surgery system of claim 17 wherein movement of the tracking device greater than a predetermined magnitude results in an error condition being signaled to the surgeon.

21. An image guided surgery system comprising:
 an imaging device having an x-ray source and an x-ray receiver for generating a plurality of two-dimensional images of a body part;
 a localizing device for determining the three-dimensional poses of the imaging device and a surgical tool;
 an imaging model with imaging model parameters for modeling the projection and mapping of points in the x-ray beam of the imaging device to the images wherein the imaging model parameters are dependent on the pose of the imaging device;
 first means for determining first imaging model parameters while the imaging device occupies a pose;
 storage means for storing a set of the first imaging model parameters and corresponding imaging device pose for a plurality of imaging device poses;
 second means for determining second imaging model parameters corresponding to a given pose of the imaging device and calculated from the set of first stored imaging model parameters and corresponding imaging device poses;
 wherein the imaging model and the second imaging model parameters for the given pose permit accurate superposition of a representation of the surgical tool on the images of the body part.

22. The image guided surgery system of claim 21 wherein the imaging device is a C-arm fluoroscope.

23. An image guided surgery system of claim 22 wherein the x-ray receiver is a flat panel imager and the imaging model parameters comprise conic projection model parameters and the set of first imaging model parameters comprise a set of first conic projection model parameters wherein appropriate second conic projection model parameters for a given pose during surgery are calculated by interpolation of a subset of the set of first conic projection model parameters.

24. The image guided surgery system of claim 21 wherein the x-ray receiver comprises a flat panel x-ray imager.

25. The image guided surgery system of claim 24 wherein the flat panel imager is integral to the imaging device.

26. The image guided surgery system of claim 24 wherein the flat panel x-ray imager is contained in a housing and said housing is attached to the imaging device.

27. The image guided surgery system of claim 2 wherein the imaging model parameters comprise conic projection model parameters and the first means for determining said conic projection model parameters comprises:
 a calibration grid having markers disposed in fixed and known locations, visible in x-ray images; and
 means for determining the pose of the calibration grid relative to either the x-ray source or x-ray receiver;
 wherein the calibration grid is held in one or more poses between the x-ray source and x-ray receiver.

28. The image guided surgery system of claim 21 wherein the first means for determining the first imaging model parameters comprises:
 a calibration grid having markers disposed in fixed and known locations, visible in x-ray images; and
 means for determining the pose of the calibration grid relative to either the x-ray source or x-ray receiver;

wherein the calibration grid is held in one or more poses between the x-ray source and x-ray receiver.

29. The image guided surgery system of claim 28 wherein the means for determining the pose of the calibration grid relative to the imaging device comprises a localizing device.

30. The image guided surgery system of claim 28 further comprising a mounting means for holding the calibration grid in a fixed and known pose relative to the imaging device.

31. An image guided surgery system with the set of first imaging model parameters of claim 21 wherein appropriate second imaging model parameters for a given pose are calculated by interpolation of a subset of the set of first imaging model parameters.

32. The image guided surgery system of claim 21 wherein the pose of the imaging device is calculated relative to a horizontal plane.

33. The image guided surgery system of claim 32 wherein the localizing device comprises a sensor unit, and said sensor unit is attached to a cart by a rigid support structure of known geometry and dimensions, such that the sensor unit's orientation relative to the horizontal plane is known.

34. The image guided surgery system of claim 32 wherein the localizing device comprises a sensor unit, and said sensor unit is attached to a cart by a rigid support structure of known geometry and dimensions and adjustable joints with rotary position encoders for measuring the angular position of each joint such that the sensor unit's orientation relative to the horizontal plane is known.

35. The image guided surgery system of claim 32 wherein the localizing device comprises a sensor unit and the orientation of the sensor unit relative to the horizontal plane is determined by an inclinometer mounted on said localizer sensor unit.

36. The image guided surgery system of claim 32 wherein the orientation of the imaging device relative to the horizontal plane is calculated by inclinometers mounted on the imaging device.

37. The image guided surgery system of claim 21 wherein the imaging model parameters comprise mapping model parameters and the first means for determining said mapping model parameters comprises:
   a calibration grid having markers, visible in x-ray images;
   means for determining the positions of the markers in the x-ray images; and
   means for determining the positions of the markers relative to the x-ray receiver;
   wherein the calibration grid is held in proximity to the x-ray receiver.

38. A computer assisted surgery apparatus to enable a surgeon to align a first surgical tool with a second surgical tool, comprising:
   a first surgical tool and a second surgical tool;
   a localizing device for determining the pose of a first coordinate frame associated with the first surgical tool and the pose of the second surgical tool;
   means for displaying representations of the two surgical tools relative to one another;
   means for generating a computer model relating a graphic representation of the first surgical tool to the first coordinate frame associated with the first surgical tool;
   means for determining the pose of a picture plane relative to the first surgical tool;
   means for projecting the representation of the first surgical tool onto the picture plane for display on the display means; and
   means for superimposing the representation of the second surgical tool over the projected representation of the second surgical tool.

39. The computer assisted surgery apparatus of claim 38 wherein the first surgical tool is attached in a fixed and known relationship to an implant or other object.

40. A computer assisted surgery apparatus to enable a surgeon to align a first surgical tool with a second surgical tool, comprising:
   a first surgical tool and a second surgical tool;
   a localizing device for determining the poses of the first and second surgical tools; and
   means for displaying representations of the two surgical tools relative to one another;
   wherein an axis of the first surgical tool is to be aligned along a line between a point on the first surgical tool and a reference point on the second surgical tool, and wherein a picture plane is defined that is perpendicular to said line and contains the reference point of the second surgical tool, and wherein alignment representations corresponding to the reference point on the second surgical tool and the intersection of said axis of the first surgical tool with the picture plane are displayed, such that the alignment representations are coincident when said axis of the first surgical tool passes through the reference point of the second surgical tool.

41. The computer assisted surgery apparatus of claim 40 further comprising means for displaying the distance from a point on the first surgical tool to the reference point of the second surgical tool.

42. An image guided surgery system to enable a surgeon to move one or more surgical tools into a desired pose relative to a body part, comprising:
   an imaging device for generating a plurality of images of the body part;
   a plurality of tracked objects and a first tracked object is a surgical tool;
   a localizing device comprising one or more controllers and two or more sensor units, each with an associated coordinate frame and comprising a plurality of individual sensor elements and each sensor unit capable of providing sufficient data to permit the calculation of the poses of the tracked objects;
   means for determining the poses of the tracked objects based on the data from one or more sensor units;
   means for displaying representations of the surgical tool relative to images of the body part; and
   means for determining the relationship among the coordinate frames of the sensor units.

43. The image guided surgery system of claim 42 wherein the pose of the surgical tool is read from a first sensor unit, and a second tracked object is the imaging device whose pose is read from a second sensor unit.

44. The image guided surgery system of claim 42 wherein the pose of the surgical tool or a second tracked object is determined from data from a first sensor unit, data from a second sensor unit, or simultaneous data from more than one sensor unit.

45. The image guided surgery system of claim 42 wherein the sensor elements are mounted on the ceiling of an operating room.

46. The image guided surgery system of claim 42 wherein the means for determining the relationship among the coordinate frames of two or more sensor units comprises:

a registration object having a plurality of localizing emitters in a fixed and known relationship and spaced such that one or more localizing emitters are visible to two or more sensor units substantially simultaneously; and means to calculate the relationship between the two or more sensor units from the registration object pose or poses as calculated from data from each of the sensor units.

47. An image guided surgery system to enable a surgeon to verify the accuracy of superpositioning a representation of a surgical tool on an image comprising:

an imaging device for generating a plurality of images;

one or more surgical tools whose poses relative to the imaging device can be tracked by a localizing device;

means for recording the pose of a surgical tool substantially simultaneous to the acquisition of an image of the surgical tool; and means for calculating and displaying a representations of the surgical tool at the recorded pose relative to the image of the surgical tool;

whereas the surgeon has sufficient time to determine the accuracy with which the surgical tool in the image is overlaid by the representation of the surgical tool at its recorded pose.

48. The image guided surgery system of claim 47 further comprising a timer of predetermined value for providing the surgeon with said sufficient time to determine the accuracy of the system.

49. The image guided surgery system of claim 47 further comprising means for allowing the surgeon to enable or disable the display of the representation of the surgical tool at its recorded pose.

50. An image guided surgery system to enable a surgeon to move one or more hand-held instruments into a desired pose relative to a body part, comprising:

a surgical tool whose pose can be tracked by a localizing device;

a display device having a screen defining a plane in a known pose relative to the localizing device;

means for calculating the pose of the surgical tool and for calculating the location where the trajectory of a specified axis of the surgical tool intersects the plane of the display device;

means for comparing the location of the intersection with locations of predefined fields in the plane of the display device; and means for initiating an action associated with each field if an activation criterion is met;

wherein the surgeon may provide input to the system via selection of a predefined field and satisfaction of the activation criterion.

51. The image guided surgery system of claim 50 wherein the activation criterion comprises the activation of a button, trigger, switch, or voice activated switch.

52. The image guided surgery system of claim 50 wherein the activation criterion comprises the continued selection of a field for a specified period of time.

53. The image guided surgery system of claim 50 wherein the activation criterion comprises performance of a characteristic tool motion.

54. An image guided system to enable an operator to move one or more tools into a desired pose relative to a work piece, comprising:

an imaging device for generating a plurality of two-dimensional images of a work piece, said imaging device including an x-ray generator and a flat panel x-ray imager;

at least one tool;

a localizing device for measuring the three-dimensional pose of the tool; and a means for displaying representations of the three-dimensional pose of the tool relative to the two-dimensional images of the work piece.

* * * * *